(12) United States Patent
Zou et al.

(10) Patent No.: US 8,388,670 B1
(45) Date of Patent: Mar. 5, 2013

(54) SENSOR/LEAD SYSTEMS FOR USE WITH IMPLANTABLE MEDICAL DEVICES

(75) Inventors: Yongning Zou, Valencia, CA (US); James B. Hamilton, Canyon Country, CA (US); Alan B. Vogel, Saugus, CA (US); Chris Sorensen, Valencia, CA (US); Ryan Albu, Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 753 days.

(21) Appl. No.: 11/623,663

(22) Filed: Jan. 16, 2007

(51) Int. Cl.
*A61F 7/00* (2006.01)
(52) U.S. Cl. ...................................................... 607/112
(58) Field of Classification Search .................... 607/122
See application file for complete search history.

(56) References Cited

U.S. PATENT DOCUMENTS

| | | | |
|---|---|---|---|
| 3,421,512 A | | 1/1969 | Frasier |
| 3,842,843 A | | 10/1974 | Mourot |
| 3,861,397 A | | 1/1975 | Rao et al. |
| 3,884,243 A | | 5/1975 | Cywinski |
| 3,897,267 A | | 7/1975 | Tseung |
| 3,941,135 A | | 3/1976 | von Sturm et al. |
| 4,628,934 A | | 12/1986 | Pohndorf et al. |
| 4,712,555 A | | 12/1987 | Thornander et al. |
| 4,730,389 A | * | 3/1988 | Baudino et al. ............... 29/825 |
| 4,788,980 A | | 12/1988 | Mann et al. |
| 4,791,935 A | * | 12/1988 | Baudino et al. ............... 600/333 |
| 4,807,629 A | | 2/1989 | Baudino et al. |
| 4,813,421 A | | 3/1989 | Baudino et al. |
| 4,858,611 A | | 8/1989 | Elliott |
| 4,877,032 A | | 10/1989 | Heinze et al. |
| 4,940,052 A | | 7/1990 | Mann et al. |
| 4,944,298 A | | 7/1990 | Sholder |
| 4,967,755 A | | 11/1990 | Pohndorf |
| 5,040,538 A | * | 8/1991 | Mortazavi ..................... 600/333 |
| 5,275,171 A | * | 1/1994 | Barcel .......................... 607/122 |
| 5,405,364 A | * | 4/1995 | Noren et al. .................... 607/17 |

(Continued)

FOREIGN PATENT DOCUMENTS

| EP | 0257954 | 3/1988 |
|---|---|---|
| WO | WO03/019170 A1 | 3/2003 |

(Continued)

OTHER PUBLICATIONS

Cassel, John et al., "Bioelectrical energy sources for cardiac pacemakers," J Assoc Adv Med Instrum. Sep.-Oct. 1972;6(5):329-334.

(Continued)

*Primary Examiner* — Eric D Bertram
*Assistant Examiner* — Roland Dinga

(57) ABSTRACT

Techniques are provided for equipping sensing/pacing leads with physiological sensors without requiring additional conductors within the leads. In a bipolar lead example for use with a pacemaker, a sensor is connected between tip and ring conductors of the lead. The sensor is configured to be activated only in response to enhanced pacing pulse (EPPs) having magnitudes or durations greater than typical pacing pulses or in response to impedance detection pulses (IMPs). In a unipolar example, the sensor is connected to the tip conductor and includes an output terminal on the external housing of the lead for providing a return current path to the pacemaker. The sensor of the unipolar lead is likewise configured to respond only to EPPs or IMPs. In other examples, the sensors are configured to be fitted to the external housing of the lead and to derive power from the lead via electromagnetic induction. Still other examples include actuators rather than sensors.

13 Claims, 14 Drawing Sheets

U.S. PATENT DOCUMENTS

| | | | |
|---|---|---|---|
| 5,411,532 A * | 5/1995 | Mortazavi | 607/22 |
| 5,431,681 A | 7/1995 | Helland | |
| 5,438,987 A | 8/1995 | Thacker et al. | |
| 5,466,254 A | 11/1995 | Helland | |
| 5,476,483 A | 12/1995 | Bornzin et al. | |
| 5,531,782 A | 7/1996 | Kroll et al. | |
| 5,535,752 A | 7/1996 | Halperin et al. | |
| 5,593,430 A * | 1/1997 | Renger | 607/18 |
| 5,843,135 A | 12/1998 | Weijand et al. | |
| 5,999,848 A * | 12/1999 | Gord et al. | 607/2 |
| 6,022,963 A | 2/2000 | McGall et al. | |
| 6,038,475 A | 3/2000 | Sikorski et al. | |
| 6,093,506 A | 7/2000 | Crespi et al. | |
| 6,125,291 A | 9/2000 | Miesel et al. | |
| 6,141,588 A | 10/2000 | Cox et al. | |
| 6,144,866 A | 11/2000 | Miesel et al. | |
| 6,163,723 A * | 12/2000 | Roberts et al. | 607/18 |
| 6,294,281 B1 | 9/2001 | Heller | |
| 6,314,323 B1 | 11/2001 | Ekwall | |
| 6,409,674 B1 | 6/2002 | Brockway et al. | |
| 6,430,440 B1 | 8/2002 | McNeil, II et al. | |
| 6,473,653 B1 | 10/2002 | Schallhorn et al. | |
| 6,531,239 B2 | 3/2003 | Heller | |
| 6,591,143 B1 | 7/2003 | Ekwall | |
| 6,658,292 B2 | 12/2003 | Kroll et al. | |
| 6,712,772 B2 | 3/2004 | Cohen et al. | |
| 6,824,521 B2 | 11/2004 | Rich et al. | |
| 6,885,889 B2 | 4/2005 | Chinchoy | |
| 7,018,735 B2 | 3/2006 | Heller | |
| 7,200,439 B2 | 4/2007 | Zdeblick et al. | |
| 2003/0167081 A1 | 9/2003 | Zhu et al. | |
| 2004/0215279 A1 | 10/2004 | Houben et al. | |
| 2004/0241537 A1 | 12/2004 | Okuyama et al. | |
| 2004/0245101 A1 | 12/2004 | Willner et al. | |
| 2005/0113987 A1 | 5/2005 | Fink et al. | |
| 2005/0159800 A1 | 7/2005 | Marshall et al. | |
| 2006/0136004 A1 | 6/2006 | Cowan et al. | |
| 2006/0159981 A1 | 7/2006 | Heller | |
| 2006/0269826 A1 | 11/2006 | Katz et al. | |
| 2008/0065051 A1 | 3/2008 | Williams | |

FOREIGN PATENT DOCUMENTS

| | | |
|---|---|---|
| WO | 03106966 A2 | 12/2003 |
| WO | 03106966 A3 | 7/2004 |
| WO | WO2004/079848 A2 | 9/2004 |
| WO | WO2004/079848 A3 | 9/2004 |
| WO | WO2004/096344 | 11/2004 |
| WO | 2004096344 A3 | 1/2005 |
| WO | WO2005/051481 | 6/2005 |
| WO | 2005096430 A1 | 10/2005 |
| WO | WO2006/045073 A1 | 4/2006 |
| WO | WO2006069215 A2 | 6/2006 |
| WO | 2006069215 A3 | 6/2009 |

OTHER PUBLICATIONS

Fontenier, Guy Ph.D., I.S.E.N. et al., "Long-term in vivo behavior of a platinum endoauricular-magnesium hybrid battery," Med Instrum. Jul.-Aug. 1975;9(4):171-176.

Fontenier, G. et al., "Coating evolution with an implantable biological battery," Biomed Eng. Aug. 1976;8(11):273-277.

Fontenier, G. et al., "Design of Experimentation with a Platinum-Magnesium Bioelectric Battery," Biomater Med Dev Artif Organs. 1975;3(1):25-45.

NonFinal Office Action, mailed Jul. 27, 2011—Related U.S. Appl. No. 11/940,552.

Restriction Requirement, mailed Nov. 16, 2009—Related U.S. Appl. No. 11/737,307.

NonFinal Office Action, mailed Apr. 6, 2010—Related U.S. Appl. No. 11/737,307.

Final Office Action, mailed Sep. 7, 2010—Related U.S. Appl. No. 11/737,307.

Advisory Action, mailed Nov. 18, 2010—Related U.S. Appl. No. 11/737,307.

* cited by examiner

SENSOR/LEAD SYSTEMS FOR USE WITH IMPLANTABLE MEDICAL DEVICES

FIELD OF THE INVENTION

The invention generally relates to implantable medical devices and in particular to lead systems and physiological sensors for use therewith.

BACKGROUND OF THE INVENTION

A variety of implantable medical devices have been developed to support various body functions. Examples of these devices include implantable pacemakers and implantable cardioverter/defibrillators (ICDs) for monitoring and for stimulating ailing hearts. Implantable bladder stimulators provide electrical stimuli to bladder muscles to restore bladder function. Similar types of electrical stimuli provided by bone growth stimulators help the patients with complicated bone fractures. Cerebellar implantable devices monitor brain activities and stimulate the brain to control seizures in epilepsy as well as pain.

Often implantable medical devices are provided with one or more leads for implant with particular organs for sensing signals therein and for delivering therapeutic stimulation. In the case of a pacemaker or ICD, the leads have electrodes for mounting within the chambers of the heart. The electrodes allow electrical cardiac signals to be sensed within the heart and further allow pacing pulses or other therapeutic stimulation pulses and shocks to be delivered directly to the heart. State-of-the-art pacemakers and ICDs are typically equipped with two or three leads, each having two or more small electrodes for pacing/sensing as well as at least one larger coil electrode for delivering powerful cardioversion or defibrillation shocks. Insofar as pacing/sensing is concerned, some leads are "unipolar," i.e. the lead includes only a single pacing/sensing electrode, referred to as a tip electrode. Electrical cardiac signals are sensed between the tip electrode and the housing of the device. Pacing pulses are also delivered between the tip electrode and the device housing. A single conductor is provided within the lead to conduct electrical signals to/from the tip electrode. Other leads are "bipolar," i.e. the lead includes a pair of pacing/sensing electrodes, referred to as tip and ring electrodes. Electrical cardiac signals are sensed between the tip and ring electrodes of the lead. Pacing pulses are also delivered between the tip and ring electrodes of the lead. Two isolated conductors are provided within the lead to separately conduct electrical signals to/from the tip and ring electrodes. These conductors are in addition to any conductors provided for connection to the separate coil electrodes. Further information regarding lead/sensor designs may be found in: U.S. Pat. No. 5,275,171 to Barcel, entitled "Implantable Lead and Sensor"; U.S. Pat. No. 5,431,681 to Helland, entitled "Combination Pacing and Defibrillating Lead Having Sensing Capability"; U.S. Pat. No. 5,438,987 to Thacker, et al., entitled "Implantable Lead for Sensing a Physiologic Parameter of the Body"; and U.S. Pat. No. 6,591,143 to Ekwall, entitled "Bending Sensor for an Implantable Lead and a Heart Stimulator with a Lead having such a Sensor."

In many cases, it is also desirable to equip the lead with one or more physiological sensors for sensing various other signals or parameters of interest. In the case of a pacemaker or ICD, physiological sensors may be provided, e.g., for sensing the oxygen content of blood, the pH of blood, the temperature, blood glucose levels, pressure, etc. Within conventional leads, each sensor requires one or more dedicated conductors for feeding power and control signals to the sensor and for receiving physiological output signals from the sensor (such as signals representative of blood glucose levels, pH levels, etc.) The addition of these conductors within the lead further requires additional connectors/filters within the device itself, such as electromagnetic interference (EMI) filters, and also reduces lead flexibility. Hence, even the addition of a single sensor to the lead significantly increases the complexity of both the lead and the device, thus elevating design and fabrication costs while potentially reducing reliability. The addition of two or more sensors on a single lead still further inflates cost and complexity. As a result, pacemaker and ICD manufacturers often do not provide sensors on leads. Hence, the patient does not benefit from the many advantages that such sensors would provide. As just one example, the provision of a blood glucose sensor on the lead would allow the pacemaker or ICD to easily detect hypoglycemia, hyperglycemia, or other blood glucose level-based conditions, provide suitable warning signals, and control therapy in response thereto.

Accordingly, it would be desirable to provide techniques for accommodating one or more sensors within implantable leads without requiring additional conductors along the leads and the corresponding additional connectors/filters needed within the device itself. It is to this end that the invention is generally directed.

Some attempts have been made to reduce the number of conductors associated with physiological sensors within leads. See, for example, U.S. Pat. No. 6,163,723 to Roberts et al., entitled "Circuit and Method for Implantable Dual Sensor Medical Electrical Lead," which describes a unipolar lead arrangement wherein only a single additional conductor is required within the lead to accommodate a pair of sensors. Briefly, a pair of physiological sensors is coupled between a standard tip lead conductor and an additional return path conductor. As best as can be understood from the descriptions, pacing pulses are delivered via the tip electrode only while the return path conductor within the lead is electrically disconnected. As such, the only return path from the tip electrode to the device is through patient tissue, allowing the therapeutic pacing pulses to be delivered to the tissue. Sensing of electrical cardiac signals via the tip electrode is also performed while the return path conductor within the lead is disconnected. To sense physiological parameters using the physiological sensor, the return path conductor of the lead is instead electrically connected, such that a complete circuit is provided through the sensors. Electrical current is then routed through the pair of sensors and directly back to the device via the return path electrode. The polarity of the current is switched to alternatingly activate just one of the sensors. In other words, only one sensor can be activate at any given time. Moreover, when the sensors are active, therapy cannot be delivered via the tip electrode, and vice versa.

As can be appreciated, there are certain potential disadvantages with this approach. The two sensors cannot be used simultaneously. In some cases, it may be desirable to sense two separate physiological parameters concurrently. Moreover, physiological sensing cannot be performed while pacing pulses are concurrently being delivered. Again, circumstances may arise where it is desirable to sense physiological parameters at the same time that a pacing pulse is delivered. Still further, the approach seems to require an even number of sensors (i.e. two per each additional return path conductor). In many cases, it is desirable to provide only a single physiological sensor, or some other odd number of sensors. Perhaps even more significantly, the technique requires additional return path conductors (one per each pair of physiological sensors). It would be far preferable to accommodate physiological sensors without requiring any additional conductors whatsoever within the lead.

Note also that some techniques have been developed that exploit bus-type arrangements to accommodate multiple sensors within a single lead. See, for example, U.S. Pat. No. 5,593,430 to Renger, entitled "Bus System for Interconnecting an Implantable Medical Device with a Plurality of Sensors" and U.S. Pat. No. 5,999,848 to Gord et al, entitled "Daisy Chain Sensors and Stimulators for Implantation in Living Tissue". These patents describe lead arrangements wherein a pair of additional conductors is provided within a lead for accommodating a set of sensors. Bus-type control schemes are employed to separately and individually activate and control the various sensors. Although only two additional conductors are required within the lead to accommodate an arbitrarily large number of sensors, these conductors are in addition to the tip and ring conductors, which are used for pacing/sensing via the tip/ring electrodes. Again, it would be far preferable to accommodate physiological sensors without requiring any additional conductors within the lead.

One design that succeeded in eliminating the need to provide an additional conductor is described in U.S. Pat. No. 5,411,532 to Mortazavi, entitled "Cardiac Pacemaker having Integrated Pacing Lead and Oxygen Sensor." Briefly, an oxygen sensor is coupled along a conductor leading to a pacing electrode. That is, the sensor is electrically connected in series with the pacing electrode along a single conduction path leading from the device through the sensor to the stimulation electrode and then back to the device via tissues of the body. The oxygen sensor is configured to receive and respond to current pulses having a polarity opposite that of pacing pulses applied to the heart muscle. A diode distinguishes between pacing pulses and oxygen sensing pulses according to the direction of current flow. Although the series design of Mortazavi advantageously allows a physiological sensor to be provided within the lead without requiring additional conductors, it does not permit the physiological sensor to sense signals during delivery of a pacing pulse. Also, it does not appear that any additional physiological sensors can be readily accommodated. Also pacing pulse amplitudes would be decreased by a diode drop, thus reducing pacing efficiency. It would be preferable to accommodate multiple physiological sensors without requiring any additional conductors within the lead.

SUMMARY OF THE INVENTION

In a system embodiment, a lead is provided for use with an implantable medical device for implant within patient tissue. The lead includes a stimulation electrode positioned adjacent to patient tissue and a conductor operative to conduct electrical current from the implantable medical device through the lead to the stimulation electrode, with the current returning to the implantable medical device along a return conduction path. The lead also includes at least one electrical device connected between the conductor and the return conduction path, so that the electrical device and the stimulation electrode are connected in parallel between the conductor and the return path. The electrical device may be a physiological sensor, such as a blood oxygen sensor, a pH sensor, a temperature sensor, a blood glucose sensor, an accelerometer, a pressure sensor, a cardiac output sensor, and an acoustic sensor, or may be an actuator, such as an implantable drug pump. Two or more sensors or actuators may be provided, each connected in parallel with each other and with the stimulation electrode. Herein, the term "patient tissue" encompasses patient fluids such as blood and so the stimulation electrode may be positioned adjacent to, or in, patient fluids. Also, herein, circuit elements are said to be "in parallel" if they are connected so that the current divides between them and later reunites.

By connecting electrical devices in parallel with the stimulation electrode, rather than in series, two or more such devices can be readily accommodated along the same conductor of the lead. Moreover, depending upon the particular implementation, the devices can be operated during delivery of a therapeutic stimulation pulse. Indeed, the same electrical pulse used to deliver stimulation to patient tissues can be used, in some implementations, to also power the electrical devices. Furthermore, by connecting each of the electrical devices between the conductor and the common return path, additional return path conductors are not required. Hence, two or more physiological sensors or actuators can be added to the lead without requiring even one additional conductor, thereby greatly reducing the size and complexity of the lead itself, as well as the size and complexity of the lead connector of the implantable medical device to which it is to be connected, while also maintaining lead flexibility.

In a unipolar lead example for use with a pacemaker, the stimulation electrode is a tip electrode and the return conduction path to the pacemaker is through patient tissue to a return electrode connected to the housing of the pacemaker. For generality, the tip electrode of the unipolar example may also be referred to herein a "first" electrode. A physiological sensor is mounted to the unipolar lead. The sensor and the tip electrode are connected in parallel between the tip conductor of the lead and the return path within patient tissue. That is, the sensor has a first, input terminal connected to the tip conductor within the lead and a second terminal placed in contact with patient tissue, such as an output terminal. To sense physiological parameters, electrical current passes from the pacemaker through the tip conductor and into the sensor via its input terminal. The current then returns to the pacemaker via patient tissues, which are in contact with both the second terminal (or "indifferent" electrode) of the sensor and the return electrode of the housing of the pacemaker. (Note that, depending upon the polarity of the system, current may instead flow in the opposite direction.) As the current passes through the physiological sensor, it powers the operation of the sensor. Output signals generated by the sensor are communicated to the pacemaker either via wireless communication (if the sensor is so equipped) or via the conduction path. If the return conduction path is used, the sensor may be equipped to convert a voltage signal representative of sensed physiological parameters into a frequency signal for transmission to the pacemaker along the return conduction path. Alternatively, the sensor is instead equipped to convert the voltage signal representative of sensed physiological parameters into digitally encoded signals (such as pulse code modulation (PCM) signals) for transmission to the pacemaker, likewise along the return conduction path. Alternatively, phase modulation may be employed.

In the unipolar example, current can also pass from the conductor into patient tissue via the tip electrode, and then back to the housing of the pacemaker. Whether the current flows through the sensor, through the tip electrode, or both depends, in part, on the relative impedance of the two current paths. Preferably, the sensor is positioned and configured to provide a lower impedance path back to the pacemaker housing, but only while the sensor is activated. Hence, while the sensor is activated, the current path through the sensor has the lower impedance and so current flows largely through the sensor. If the sensor is not activated, the current path through the tip electrode thereby has the lower impedance and so current flows through the tip electrode but not through the sensor. This allows current to be selectively directed by the pacemaker either through the tip electrode or through the sensor. In this regard, the sensor is preferably configured to be activated only in response to a voltage exceeding some activation threshold. The pacemaker is programmed to selectively deliver either low voltage pacing pulses (i.e. pulses having voltages below the activation threshold) and higher voltage control pulses (i.e. pulses having voltage above the activation threshold). The higher voltage pulses are referred to herein as enhanced pacing pulses (EPPs). As such, the lower voltage pacing pulses do not activate the sensor or even pass through the sensor. Instead, pacing pulses simply pass through the tip electrode and back to the device housing via patient cardiac tissue, as with conventional unipolar pacing pulses. In this manner, conventional unipolar pacing is accommodated. The higher voltage EPPs, in contrast, have sufficient voltage to activate the sensor and thereby redirect current away from the tip electrode and through the sensor. The activation threshold need not be a programmable threshold. Rather, typically, the threshold is simply a fixed threshold specified by the choice of electrical components of the sensor (such as the choice of particular transistors, breakdown diodes, or the like.)

As such, EPPs do not pass through tip electrode but instead pass substantially only through the sensor, so as to provide adequate power for the sensor. Note that, depending upon the timing of the EPP, the voltage thereby established between the second, output terminal of the sensor and the device housing during the EPP may serve to also depolarize cardiac tissue. More specifically, EPPs delivered to the sensor while cardiac tissue is not refractory may be advantageously used both to power the sensor and also to pace the heart. As can be appreciated, the delivery of any such dual pacing/control EPPs should be timed in accordance with otherwise conventional pacing techniques by taking into account atrioventricular (AV) delays and the like. In contrast, EPPs delivered to the sensor while cardiac tissue is still refractory will not pace the heart.

Hence, by controlling the timing of the delivery of the EPPs within this particular unipolar example, the EPPs can selectively be used either to just power the physiological sensor or to both power the sensor and simultaneously deliver pacing therapy. In other words, in cases where it is desirable to sense physiological parameters while a pacing pulse is delivered, the pacemaker preferably delivers an EPP via the unipolar lead while cardiac tissue is not refractory. This pulse will pace the heart and simultaneously activate the sensor to sense physiological parameters. In cases where it is instead desirable to sense physiological parameters after a pacing pulse is delivered, the pacemaker preferably delivers a low voltage pacing pulse while cardiac tissue is not refractory to depolarize the tissue. The pacemaker then delivers the higher voltage EPP during a subsequent refractory period so as to activate the sensor. In some implementations, the EPP is a pacing pulse having an increased pulse width rather than, or in addition to, an increased voltage. In still other unipolar implementations, impedance measurement pulses (IMPs), used to measure the electrical impedance between the heart and the pacemaker, may be additionally or alternatively used to power the sensor.

In a bipolar lead example for use with a pacemaker, the lead includes both tip and ring electrodes connected to the pacemaker via, respectively, tip and ring conductors within the lead. Hence, the return conduction path from the tip electrode back to the pacemaker is through a portion of patient tissue and then through the ring electrode and the ring conductor. For generality, the tip and ring electrodes may also be referred to herein as "first" and "second" electrodes. Depending upon the particular implementation, the first electrode may be more negative than the second, or vice versa. The physiological sensor is connected between the tip and ring conductors of the lead and so the return path from the sensor to the pacemaker is also along the ring conductor. Hence, unlike the unipolar lead example, the sensor of the bipolar lead does not utilize a second, output terminal in contact with patient tissue. (Depending upon the particular sensor, the sensor itself may employ sensing electrodes placed in contact with patient tissue, but the second, output terminal of the sensor—through which current flows back to the pacemaker—is not exposed to patient tissue.) To sense physiological parameters, electrical current passes from the pacemaker through the tip conductor and into the sensor via its input terminal. The current passes through the sensor and then returns to the pacemaker via the ring conductor. (As in the unipolar example, the polarity may be reversed so that the current flows in the opposite direction.) Current passing through the physiological sensor powers the operation of the sensor. Output signals generated by the sensor are communicated to the pacemaker either via wireless communication (if the sensor is so equipped) or via the tip and ring conductors. If the conductors are used, the sensor may be equipped to convert a voltage signal representative of sensed physiological parameters into a frequency signal for transmission to the pacemaker along the conductors. Alternatively, the sensor is instead equipped to convert the voltage signal representative of sensed physiological parameters into digitally encoded signals (such as PCM signals) for transmission to the pacemaker, likewise along the conductors. In other implementations, phase modulated signals are used. That is, a phase locked loop (PLL) or a clocking scheme is employed wherein a sensor circuit modifies a carrier wave or uses reflected impedance.

In the bipolar example, current can also pass from the tip conductor into patient tissue via the tip electrode, and then back to the pacemaker via the ring electrode and ring conductor. Whether the current flows through the sensor, through the tip/ring electrodes, or both depends, again, on the relative impedances of the two current paths. Preferably, the sensor is positioned and configured to provide a lower impedance path back to the pacemaker but, again, only while the sensor is activated. Hence, while the sensor is activated, the current path through the sensor has the lower impedance and so current flows through the tip conductor, the sensor and the ring conductor and does not reach or has very low amplitude to go through the tip/ring electrodes. If the sensor is not activated, the current path through the tip/ring electrodes thereby has the lower impedance and so current flows through patient tissues between the tip/ring electrode pair but does not flow through the sensor. As with the unipolar example, this allows current to be selectively directed by the pacemaker either through the tip/ring electrode pair or through the sensor. In this regard, the sensor is preferably configured to be activated only in response to a voltage exceeding the predetermined voltage activation threshold. The pacemaker is again programmed to selectively deliver either low voltage pacing pulses (i.e. pulses having voltages below the activation threshold) or higher voltage EPPs (i.e. pulses having voltage above the activation threshold or having an extended pulse width). As such, the lower voltage or narrower pulse-width pacing pulses do not activate the sensor or even pass through the sensor. Rather, pacing pulses pass through the tip/ring electrode pair and back to the pacemaker via the ring conductor, as with conventional bipolar pacing pulses. In this manner, conventional bipolar pacing is accommodated. The higher voltage or wider pulse-width EPPs, in contrast, have sufficient energy to activate the sensor and thereby redirect current away from the tip/ring electrode pair and through the sensor.

Thus, as with the unipolar lead, the sensor control pulses of the bipolar lead pass substantially only through the sensor so as to provide adequate power for the sensor. Unlike the unipolar lead, however, the control pulses of the bipolar lead are not capable of depolarizing cardiac tissue since the bipolar lead sensor control pulses do not pass directly through patient tissue. Hence, such control pulses need not be timed relative to refractory periods or the like. Rather, the EPPs can be delivered to the sensor via the bipolar lead at any time (other than concurrently with a low voltage pacing pulse as such would attenuate the pacing pulse and prevent it from reaching the tip/ring electrode pair). Thus, the bipolar implementation has somewhat greater flexibility insofar as timing the delivery of sensor control pulses than the unipolar embodiment, since there is no concern that such pulses will also depolarize cardiac tissue. The unipolar embodiment, however, more readily accommodates the sensing of physiological parameters during the delivery of pacing pulses, as may be advantageous in some cases depending upon the particular physiological parameter to be sensed. For example, intracardiac pressure may be sensed while a pacing pulse is being delivered. Or drug may be delivered during a pacing pulse delivery.

With either unipolar or bipolar leads, the sensor or actuator may be configured to be mounted to the exterior housing of the lead and configured to draw power from the lead via electromagnetic induction. That is, a device is provided for use with a lead of an implantable medical device for implant within patient tissue wherein the device includes a power coupler operative to receive power from the lead via electromagnetic induction and has an electrical device (such as a sensor or actuator) powered by power received by the power coupler. In this manner, a "snap-on" and/or "slip-on" sensor or actuator device is provided, such that the lead itself need not be physically modified.

In a method embodiment of the invention, a technique is provided for operating an electrical device mounted to a lead connected to an implantable medical device for implant within a patient wherein the lead also has a stimulation electrode connected to the implantable medical device via a conductor within the lead. In accordance with the technique, the electrical device and the stimulation electrode are electrically connected in parallel between the conductor and a common return conduction path. Then, a voltage differential is selectively applied between the conductor of the lead and the return conduction path, so that a voltage differential exits concurrently between the stimulation electrode and the return conduction path and between input and output terminals (or other secondary terminal) of the electrical device within the lead. Again, the electrical device may be a physiological sensor or an actuator. Two or more sensors or actuators may be provided, each electrically connected in parallel with each other and with the stimulation electrode.

As with the system embodiments discussed above, by connecting electrical devices in parallel with a stimulation electrode, rather than in series, two or more such devices can be readily accommodated along the same conductor of the lead. Also, parallel connections on a lead are generally less risky for system reliability than having series connections where any broken connection might cause the lead to be unusable. The devices, depending upon the particular implementations, can be operated during delivery of a therapeutic stimulation pulse. Furthermore, by connecting each of the electrical devices between the conductor and the common return path, additional return path conductors are not required and so two or more physiological sensors or actuators can be added to the lead without requiring any additional conductors. The method may be applied to either unipolar leads or bipolar leads in conjunction with, e.g., a pacemaker or other cardiac stimulation device.

Sensors or other electrical devices having three or more terminals may be utilized as well. For example, a three-terminal sensor may be provided for use with a bipolar lead wherein two of the terminals are used to connect the sensor between the tip (first) and ring (second) conductors of the bipolar lead for powering the sensor. A third terminal of the sensor is connected to a sensor output electrode positioned adjacent to patient tissue so that output signals from the sensor may be transmitted from the sensor to the implantable device via the patient tissue. Under the broad definition of the term "in parallel" set forth above, this embodiment presents an electrical device connected in parallel with the stimulation electrodes of the bipolar lead, even though the electrical device itself has three terminals. Other multiple terminal embodiments are encompassed by the principles of the invention as well.

Although aspects of the invention are advantageously employed with unipolar or bipolar leads used with pacemakers or other cardiac stimulation device, principles of the invention may be applied to other leads or multi-electrode systems and/or to other implantable medical devices.

BRIEF DESCRIPTION OF THE DRAWING

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. The description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Unipolar Lead Example

Figure 1:
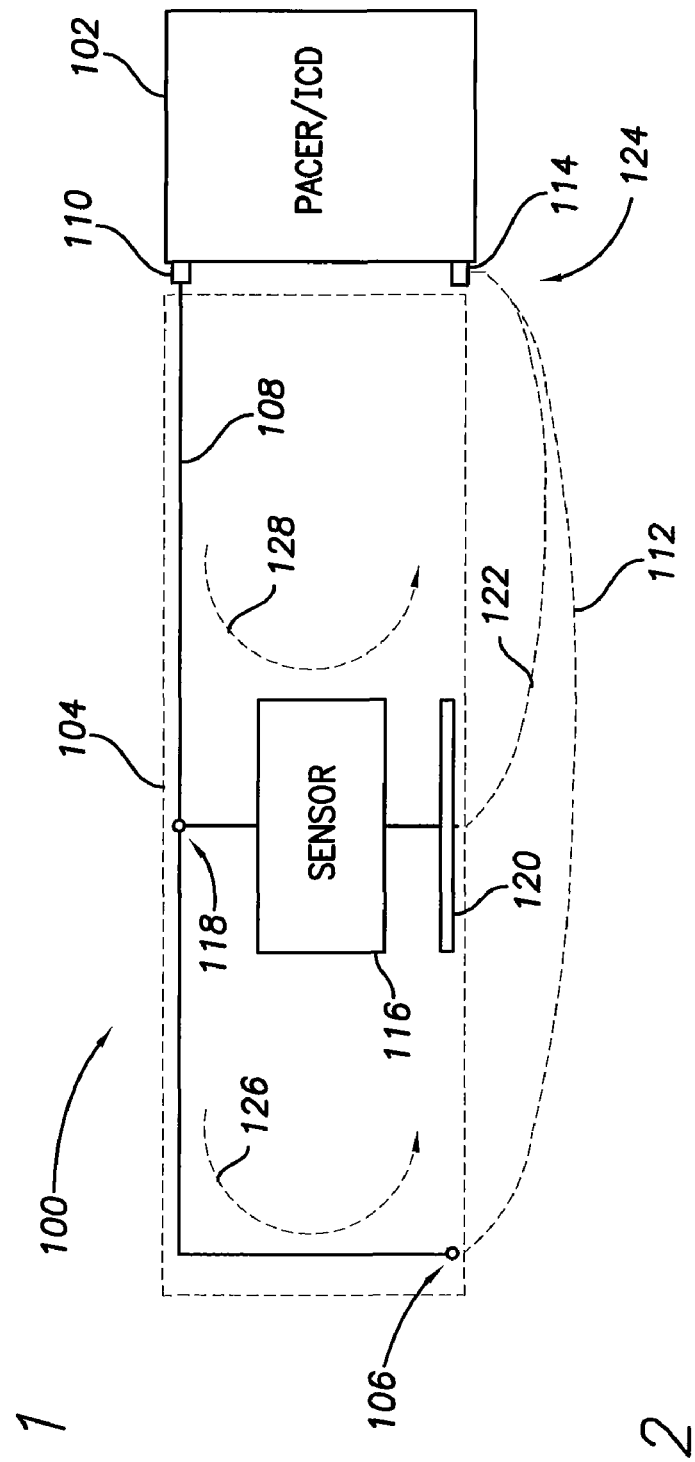
FIG. 1 is a block diagram, partly in schematic form, illustrating a unipolar lead implementation of the invention wherein a sensor is mounted to the lead without requiring an additional return conductor.
Figure 2:
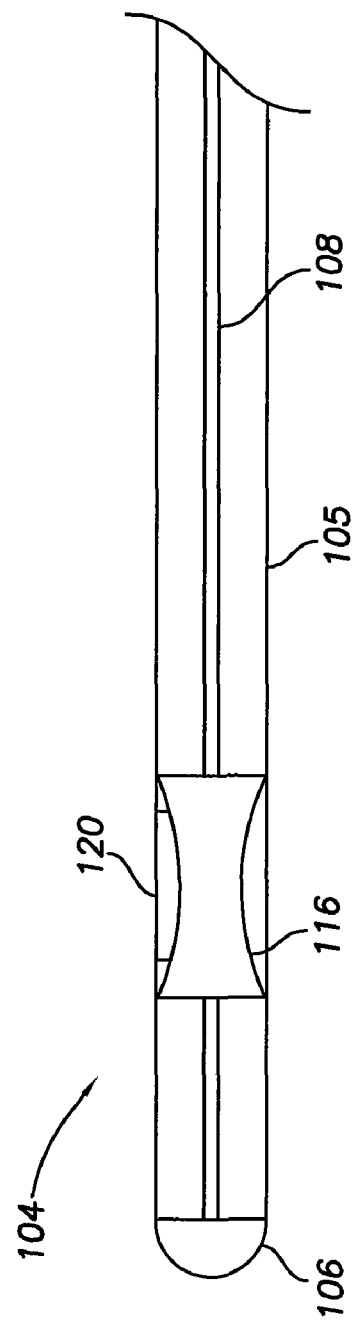
FIG. 2 is an elevational view, partly in cross section, illustrating the unipolar lead implementation of FIG. 1.

FIG. 1 schematically illustrates an implantable system 100 having a pacer/ICD, implantable pulse generator (IPG) or other implantable medical device 102 and a unipolar lead 104. FIG. 2 illustrates a physical implementation of the lead wherein components are enclosed within a sheath or housing 105. The unipolar lead includes a tip electrode 106 connected to the pacer/ICD via a tip conductor 108 coupled to a tip connector 110 of the pacer/ICD. A return path 112 from the tip electrode 106 to a return (housing) connector 114 is provided through patient tissue (typically cardiac and thoracic tissue.) For generality, tip electrode 106 of this unipolar example may also be referred to herein a "first" electrode. A physiological sensor 116 has a first (input) terminal 118 connected to the tip conductor and has a second (output) terminal 120 formed out of conductive material and placed in contact with patient tissue. A return path 122 from the sensor is provided to return electrode 114 through patient tissue. Depending upon the relative proximity of tip electrode 106 and sensor output terminal 120, return paths 112 and 122 may initially pass through somewhat different patient tissue. However, at least in proximity to the housing connector, the return paths will coincide providing a common return path portion 124. With this arrangement, the sensor and the tip electrode are thereby electrically connected in parallel between tip conductor of the lead and common return path 124. Two current paths are thereby provided between tip terminal 110 and return electrode 114. A first path 126 passes along the tip conductor through the tip electrode and back to the return electrode of the pacer/ICD via tissue return path 112. A second path 128 passes along the tip conductor through the sensor and back to the return electrode of the pacer/ICD via tissue return path 122. A voltage applied across terminals 110 and 114 by the pacer/ICD therefore generates a current along one or both of these paths, depending upon the relative impedances along the paths. Hence, electrical pacing pulses can be selectively delivered to the patient tissue by routing at least a portion of the current along path 126. The sensor can be selectively activated to sense physiological parameters of interest within the patient tissue by routing at least a portion of the current along path 128.

In one example, sensor 116 is positioned and configured to provide a lower impedance path back to the pacemaker housing but only while the sensor is activated. That is, when the sensor is activated, path 128 has a lower impedance than path 126 and so current flows through the sensor, powering its operation. The sensor is configured to be activated only in response to a voltage having a magnitude exceeding a voltage activation threshold, such as a voltage two or three times the peak magnitude of pacing pulses. Conventional pacing pulses typically have peak voltages in the range of 0.5-5 V. Hence, a sensor activation threshold voltage of 6V, or at least 1V above the regular pacing pulse amplitude, is typically appropriate. The EPP itself may have, e.g., a peak voltage of 7V or above so as to reliably activate the sensor by having a higher voltage than the threshold. (Note that control mechanisms should be in place to actively control the pacemaker's high voltage protection circuitry so that the higher voltage is not shunted on the pacing conductors. Such a protective device is known as an Input Protection Module, Transient Surge Suppressor, or protective diode network.) Similarly, for EPPs with increased pulse width, the sensor activation threshold may be defined as an appropriate pulse width, for example 1 ms, since the typical pacing pulse width range is 0.25 ms to 0.6 ms.

Figure 3:
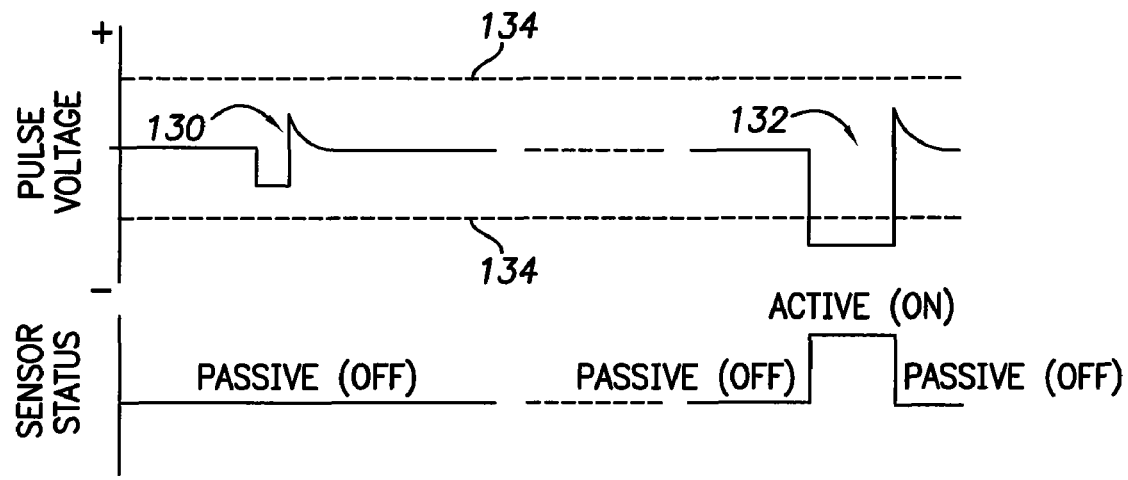
FIG. 3 is a timing diagram illustrating EPPs that may be used to power and control a lead sensor, such as the sensor of FIG. 1 or 2.

FIG. 3 illustrates a conventional (i.e. relatively low voltage) pacing pulse 130 and a higher voltage sensor control pulse 132 (herein also referred to as an EPP). An activation threshold 134 is also illustrated. (The activation threshold is a voltage magnitude and hence can be exceeded either by a relatively large negative voltage or a relatively larger positive voltage.) With a peak voltage magnitude less than the activation threshold, the conventional pacing pulse 130 does not activate the sensor of FIG. 1 or even pass through the sensor. Instead, such conventional pacing pulses simply pass along path 126 (i.e. through tip electrode 106 and back to return terminal 114 via return path 112 of patient cardiac tissue) in accordance with otherwise conventional unipolar pacing. The higher voltage EPP 132, in contrast, has sufficient voltage to activate the sensor of FIG. 1 and thereby redirect current along path 128 so as to power the sensor.

The pacer/ICD is programmed to selectively deliver either the low voltage pacing pulses (i.e. pulses having voltages below the activation threshold) or EPPs (i.e. pulses having voltage above the activation threshold) so as to control whether conventional pacing is performed or whether the sensor is activated. In FIG. 3, periods of time when the sensor is active (i.e. ON) are shown in contrast with periods of time when the sensor is passive (i.e. OFF). The duration of conventional pacing pulse 130 is typically in the range of 0.25 milliseconds (msecs) to 1.0 msecs. The duration of the EPP is considerably longer, with a programmable range of, e.g., 0.05 msec to 1.5 msec. In the example of FIG. 3, EPP 132 is set to maintain a voltage magnitude above the threshold magnitude for about 1.5 msec such that the sensor is thereby activated for that period of time. For many sensors, this is sufficient to detect a physiological parameter and communicate that parameter to the pacer/ICD. For sensors requiring more time, sequential activation techniques employing multiple pulses (discussed below) are preferably used.

Note that, in the example of FIG. 3, the EPP will likely depolarize cardiac tissue if the tissue is not refractory at the time the EPP is delivered. That is, assuming the sensor is positioned within a chamber of the heart, the voltage established between the output terminal of the sensor and the device housing during the EPP will depolarize any non-refractory cardiac tissue. (If the sensor is instead mounted to the lead at a point outside the heart, it probably would not depolarize heart tissue since the return path would not pass through cardiac tissue.) Hence, care should be taken in timing the delivery of EPPs. Triggered pacing modes such as DDT mode may be used by the pacer/ICD device to control the delivery of EPPs. In one example, the EPPs are delivered only while the cardiac tissues are refractory so that the EPPs do not depolarize those tissues. That is, in that example, only conventional pacing pulses are delivered while the tissues are non-refractory (to thereby depolarize the tissues and cause selected chambers of the heart to contract.) Typically, the EPPs are delivered immediately after a pulse, particularly if the sensor needs time to power up and measure outside of the pacing pulse. In one example, if a pressure measurement is needed 50 msec after a stimulation pulse, the EPP is timed so that there will be sufficient time for the sensor to power up to sense the pressure 50 msec after the pacing pulse. As can be appreciated, this depends on the sensor circuit implementation. If a measurement needs to be made at the beginning of a pacing pulse, the sensor should instead be powered before the therapeutic pulse arrives. As already explained, convention pulses do not activate the sensor. One or more EPPs are subsequently delivered while the tissues are refractory so as to activate the sensor to sense physiological parameters at that time. These pulses therefore have no therapeutic effect on the cardiac tissues. In a second example, EPPs are instead delivered in the place of conventional pacing pulses while cardiac tissue is non-refractory. As such, the EPP serves both to control the sensor and to depolarize cardiac tissue, i.e. the EPP is a dual pacing/control pulse. As can be appreciated, the delivery of any such dual pacing/control pulses should be timed in accordance with otherwise conventional pacing techniques by taking into account AV delays and the like.

Thus, in the unipolar example of FIG. 1, EPPs can selectively be generated by the pacer/ICD either to just power the physiological sensor or to both power the sensor and simultaneously deliver pacing therapy. In cases where it is desirable to sense physiological parameters while a pacing pulse is delivered, the pacemaker preferably delivers an EPP pulse via the unipolar lead while cardiac tissue is not refractory. This pulse will pace the heart and simultaneously activate the sensor to sense physiological parameters. In cases where it is instead desirable to sense physiological parameters after a pacing pulse is delivered, the pacemaker preferably delivers a conventional low voltage pacing pulse while cardiac tissue is not refractory to thereby depolarize the tissue. The pacemaker then delivers the EPP during the subsequent refractory period so as to activate the sensor.

Note that the activation threshold need not be a programmable threshold (although such may be provided, if desired.) Typically, the activation threshold is merely specified by the choice of components used within the circuitry of the sensor, such as the choice of transistors, breakdown diodes, comparators, etc. In other implementations, rather than having a voltage-based activation threshold, the sensor is instead configured to respond to a pulse of sufficient duration. That is, a duration-based activation threshold is provided.

The sensor of FIG. 1 can alternatively be powered via an IMP. IMPs are typically employed by pacer/ICDs to detect the impedance along the current path through the lead, tissue and back to the device housing (via the tip electrode.) Extremely high impedance indicates that the lead has probably fractured and must be repaired or replaced. Assuming that the lead has not fractured, the impedance value detected using the IMP can be used by the device to track patient respiration based on variations in the impedance caused by the expansion and contract of the chest (which affects the relative spacing between the tip electrode and the housing of the pacer/ICD as well as the fluid to air difference.) Note that IMPs are AC current pulses, not DC pulses (as with conventional pacing pulses and with EPPs.) IMPs are typically in the range of 200 microamperes ($\mu A$) to 1 milliampere (mA) and are designed to not be able to stimulate the tissue. IMPs can also be used to measure stroke volume, and long term transthoracic impedance showing lung or tissue fluid retention.

Figure 4:
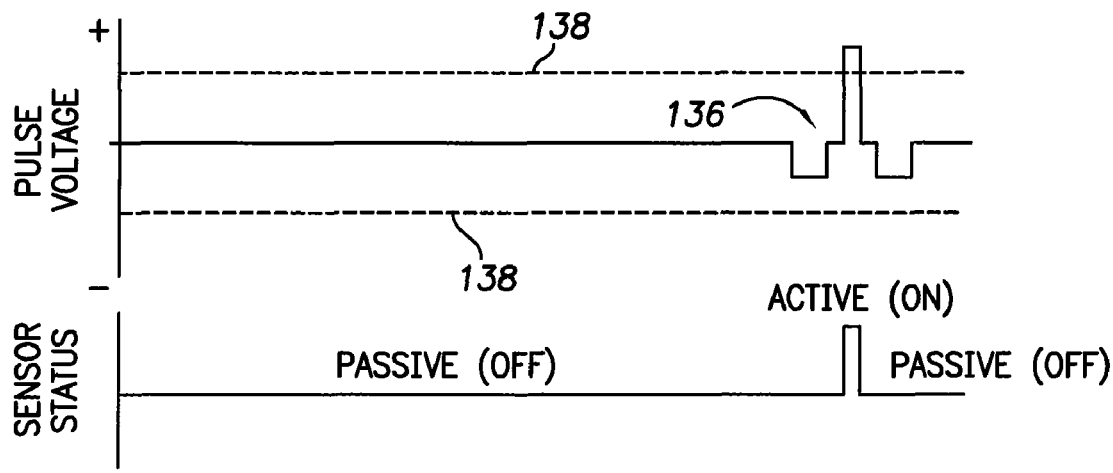
FIG. 4 is timing diagram illustrating IMPs that may be used to power and control a lead sensor, such as the sensor of FIG. 1 or 2.

With the unipolar lead of FIG. 1, the sensor is configured to be activated in response to a current exceeding a current activation threshold 138. FIG. 4 illustrates an exemplary IMP 136. The IMP 136 provides sufficient current to activate the sensor of FIG. 1 thereby redirecting current along path 128 so as to power the sensor. More specifically, the exemplary IMP has a center pulse with a current of 1 mA and has leading and trailing pulse portions providing currents of −250 $\mu A$ (i.e. the current is flowing in the opposite direction). The center pulse has a duration of 40 microseconds ($\mu S$) whereas the leading and trailing pulse portions each have pulse durations of 80 $\mu S$. The gap between the end of the leading pulse and the center pulse is 40 $\mu S$. A similar 40 $\mu S$ gap separates the center pulse and the trailing pulse. These are just exemplary parameters. With this example, the current activation threshold is set to, e.g., 0.75 mA. Pacing pulses typically deliver very little current and hence do not activate the sensor. The voltages associated with IMPs are below a depolarization threshold and hence do not interfere with pacing.

In FIG. 4, periods of time when the sensor is active (i.e. ON) are again contrasted with periods of time when the sensor is passive (i.e. OFF). Due to the much shorter duration of the IMP (as compared to the EPP of FIG. 3), the sensor remains active for a shorter period of time. In the example of FIG. 4, the IMP activates the sensor for only about 40 $\mu s$ at a time. As such, when using IMPs to power the sensor, it is often preferred to use the sequential pulse techniques employing multiple pulses discussed below. For some sensors, it may be appropriate to instead use an EPP so as to ensure the sensor has sufficient time to perform its operations. Note that, in addition to using a given IMP to power the sensor, the same IMP can potentially also be used by the pacer/ICD to detect thoracic impedance, depending upon the particular implementation of the invention. That is, the current pulse passing from the sensor back to the device housing via patient tissue can still be analyzed by the pacer/ICD to evaluate thoracic impedance. Preferably, however, sequential IMPs are used, i.e. a train of IMPs is employed to provide sufficient power to power the sensor. Also, the polarity of the first multiphased IMP pulse can be changed to either engage the sensor or disengage the sensor. Of course, the pacer/ICD is suitably programmed (in accordance with otherwise conventional techniques) to take into account the fact that the IMP (or train of IMPs) is conducted through the sensor when numerically calculating the thoracic impedance.

Bipolar Lead Example

Figure 5:
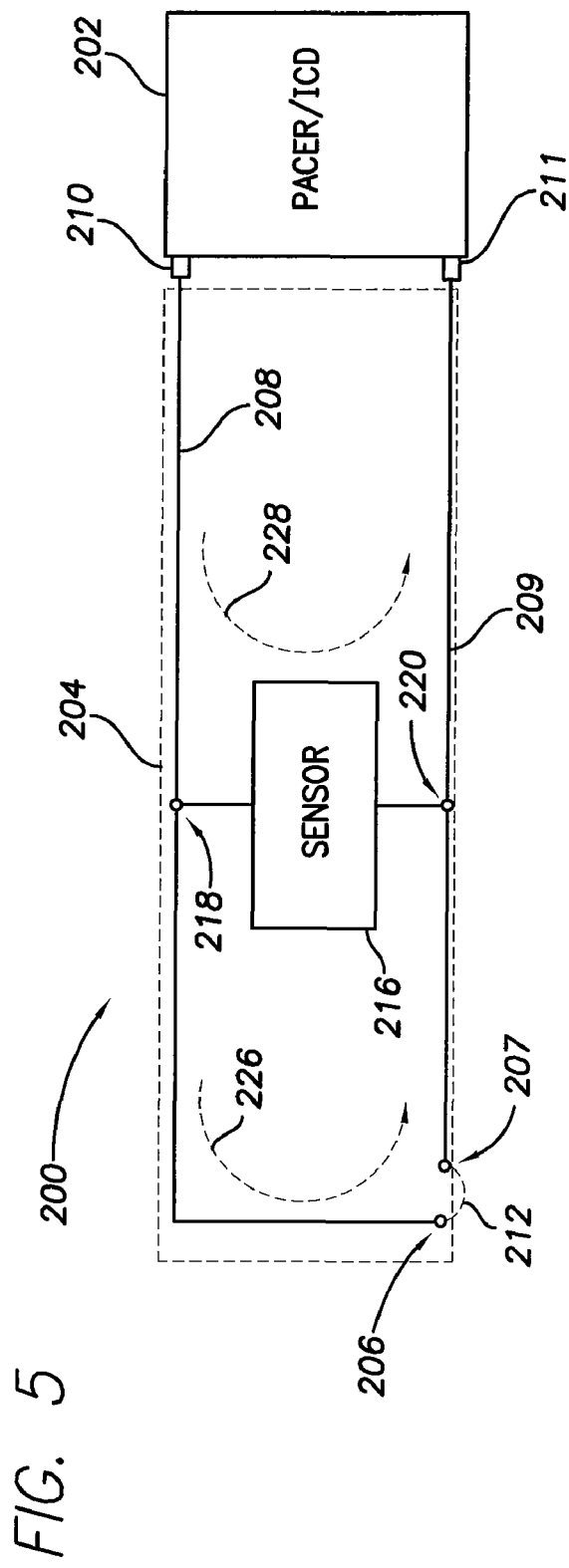
FIG. 5 is a block diagram, partly in schematic form, illustrating a bipolar lead implementation of the invention wherein a sensor is mounted to the lead without requiring an additional return conductor.
Figure 6:
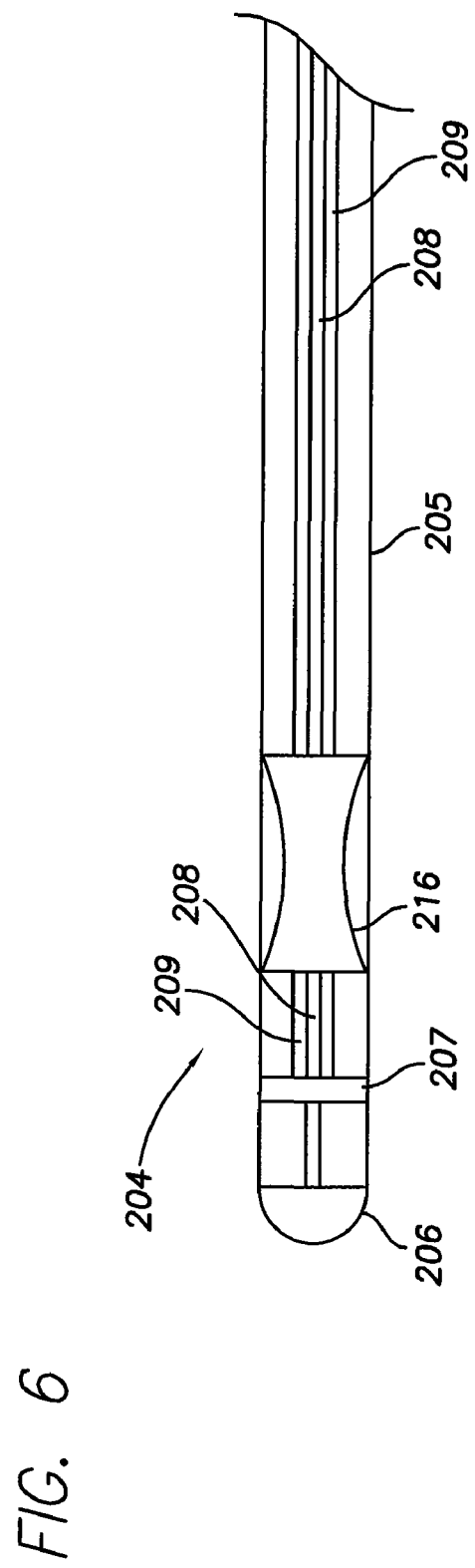
FIG. 6 is an elevational view, partly in cross section, illustrating the bipolar lead implementation of FIG. 5.

FIG. 5 schematically illustrates an implantable system 200 having a pacer/ICD or other implantable medical device 202 and a bipolar lead 204. FIG. 6 illustrates a physical implementation of the bipolar lead wherein components are enclosed within a sheath or housing 205. The bipolar lead includes a tip electrode 206 connected to the pacer/ICD via a tip conductor 208 coupled to a tip connector or terminal 210 of the pacer/ICD. The bipolar lead also includes a ring electrode 207 connected to the pacer/ICD via a ring conductor 209 coupled to a ring connector or terminal 211 of the pacer/ICD. For generality, the tip and ring electrodes may also be referred to herein as "first" and "second" electrodes. Depending upon the particular implementation, the first electrode may be more negative than the second, or vice versa. (In the illustration of FIG. 6, the tip conductor is held inside the ring conductor and is electrically isolated therefrom with appropriate insulation, not shown.) A conducting path 212 from the tip electrode 206 to a ring electrode 207 is provided through patient tissue (typically cardiac tissue.) A physiological sensor 216 has a first (input) terminal 218 connected to the tip conductor and has a second (output) terminal 220 connected to the ring conductor. A return path from the sensor to the pacer/ICD is therefore provided along ring conductor 209. With this arrangement, the sensor and the tip/ring electrode pair are thereby electrically connected in parallel between the tip conductor and the ring conductor. Two current paths are thereby provided between tip terminal 220 and ring terminal 211. A first path 226 passes along the tip conductor to the tip electrode, then passes through patient tissue before returning to the pacer/ICD via the ring electrode and the ring conductor. A second path 228 passes along the tip conductor through the sensor and back to the pacer/ICD via the ring conductor. (Depending upon the polarity, current may instead flow in the opposite direction.) A voltage applied across terminals 210 and 211 by the pacer/ICD therefore generates a current along one or both of these paths, depending upon the relative impedances along the paths. Hence, electrical pacing pulses can be selectively delivered to the patient tissue by routing at least a portion of the current along path 226. The sensor can be selectively activated to sense physiological parameters of interest within the patient tissue by routing at least a portion of the current along path 228.

Sensor 216 is preferably positioned and configured such that, while the sensor is activated, path 228 has a lower impedance than path 226 and so current flows through the sensor, powering its operation. As with the unipolar example discussed above, the sensor is configured to be activated in response to a voltage having a magnitude exceeding a predetermined voltage activation threshold. An EPP (see FIG. 3) is generated by the pacer/ICD to activate and power the sensor.

Note that, in contrast to the unipolar lead example discussed above, the EPP will not necessarily depolarize cardiac tissue even when the tissue is not refractory at the time the EPP is delivered. This is because the EPP in the bipolar lead is primarily conducted through the sensor and back to the pacer/ICD via the ring conductor without passing through cardiac tissue. Only that portion of the EPP having a voltage less than the threshold voltage will pass through the cardiac tissue. That portion may, or may not, depending upon its magnitude and duration (as well as the location of the sensor), depolarize the cardiac tissue.

As with the unipolar lead implementation, the sensor of FIG. 5 can alternatively be powered via one or more IMPs. Note that the IMPs can be controlled to be delivered to the sensor only or to tissue only. In this regard, the indifferent electrode (i.e. the output electrode of the sensor) and the case can be set at the same potential. If so, the voltage will attenuate when the sensor turns on, but the voltage may still be sufficient for the device to measure impedance if the device is calibrated for the drop in current. Indeed, if the sensor current is very small, then a single IMP may be fully useable to both power the sensor and also measure thoracic impedance.

Multiple Sensor Examples

Figure 7:
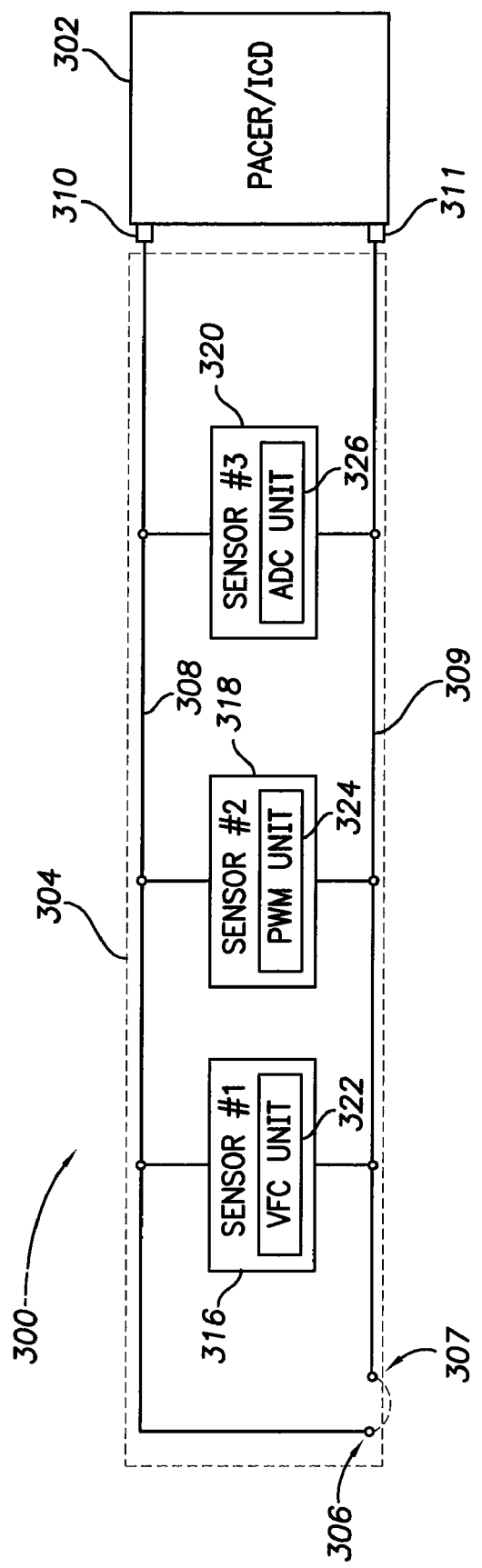
FIG. 7 is a block diagram, partly in schematic form, illustrating a bipolar lead implementation of the invention wherein multiple sensors are mounted to the lead without requiring an additional return conductor.

FIG. 7 schematically illustrates an implantable system 300 having a pacer/ICD or other implantable medical device 302 and a bipolar lead 304 fitted with three sensors. This arrangement is similar to the single sensor bipolar arrangement of FIGS. 5 and 6 and only pertinent differences will be discussed. As before, the bipolar lead includes a tip electrode 306 connected to the pacer/ICD via a tip conductor 308 coupled to a tip terminal 310 and a ring electrode 307 connected to the pacer/ICD via a ring conductor 309 coupled to a ring connector 311 of the pacer/ICD. Three physiological sensors 316, 318 and 320 are connected between the tip conductor and ring conductors. As such, the sensors are electrically connected in parallel with one another and also in parallel with the tip/ring electrode pair. The sensors are preferably configured to present about the same impedance, such that current flows more or less equally through the sensors. The sensors are also preferably configured to be activated by a voltage of about the same amount so that all three sensors are either ON or OFF at the same time. As such, when an EPP is applied, all three sensors respond by sensing (typically different) physiological parameters. When a conventional pacing pulse is generated, none of the sensors responds and the pacing pulse instead passes between the tip and ring electrodes so as to depolarize cardiac tissue.

With the sensors configured to be activated at the same time, the sensors preferably use output transmission techniques that differ from one another so as to allow the pacer/ICD to reliably decode their respective output signals. For example, the first sensor may be equipped to exploit voltage/frequency conversion (VFC). That is, the sensor includes a VFC output unit 322 for communicating output signals to the pacer/ICD as a frequency-based signal. The sensed parameter is converted to a voltage signal and then further converted into a frequency signal in the range of [$freq_1$, $freq_2$], which is subsequently capacitively or inductively coupled into the lead. The pacer/ICD receives the signal through a Band Pass Filter (BPF), not separately shown. The pacer/ICD then derives the original sensed parameter based on coefficients obtained from calibration. Calibration can be performed in house or at implant. In one example, a lookup table is provided to calibrate the sensor. That is, the lookup table relates frequency values output from the sensor to actual values of the physiological parameter being sensed, such as blood pressure values, etc. A significant advantage of the VFC method is that no analog to digital converter (ADC) is required within the sensor itself. In this regard, raw data is sent to the pacer/ICD. That is, the data does not need to be converted or processed by the sensor itself prior to transmission to the pacer/ICD. (The sensor, however, may still have an ADC for one reason or another, but does not need an ADC to convert raw data for the purposes of transmission.)

The second sensor may instead be equipped to perform pulse width modulation (PWM). That is, the sensor includes PWM output device 324 for communicating output signals to the pacer/ICD as a digital signal. The sensed parameter is converted into a PWM signal, which is sent to the pacer/ICD along the ring conductor with a carrier frequency $f_c$. The pacer/ICD uses its BPF to filter out $f_c$ and then derives the digital values encoded by the PWM signal. The value of the sensed parameter is then obtained using calibration coefficients. The third sensor may instead be equipped to communicate the sensed parameter to the pacer/ICD via serial ADC plus modulation. That is, the sensor converts the sensed parameter to a voltage signal (i.e. an analog signal). A serial ADC output unit 326 then converts the analog signal into digital values and sends the digital signals over the ring conductor via a digital bit-stream modulated by two carrier frequencies $f_1$ and $f_2$, where $f_1$ and $f_2$ are used to transmit '1' and '0', respectively. The output signal is capacitively or inductively coupled into the tip/ring conductor of the lead. In other implementations, one or more sensors may be equipped to send sensed parameters via wireless communication. Also, rather than having the various sensors use fundamentally different communication techniques, the sensors may use similar techniques but with their output signals modulated to avoid conflicts. For example, each may use VFC but with different frequency ranges.

With multiple sensors, it may be appropriate to provide an EPP having a greater magnitude so as to provide adequate power for all the sensors. In other implementations, the various sensors may be configured to respond to different voltage ranges so that they may be selectively and individually activated by the pacer/ICD. In still other implementations, the sensors may be configured to respond only to a series of different activation/deactivation pulse sequences to again permit the pacer/ICD to separately activated and deactivate the various sensors. Bus techniques, such as those used in the patents discussed above, may potentially be employed (with the bus signals carried over the tip/ring conductors rather than over dedicated conductors as described in those patents.) In general, any appropriate time-division or frequency-division multiplexing scheme may be employed.

As with the implementations discussed above, the multiple sensors of FIG. 7 can alternatively be powered via IMPs, assuming that the sensors are suitably configured and assuming that a sufficient amount of power is thereby provided to the sensors via the IMPs. In other examples, some sensors are equipped to respond to EPPs, whereas others are equipped to respond to IMPs.

Sequential Sensor Control

Figure 8:
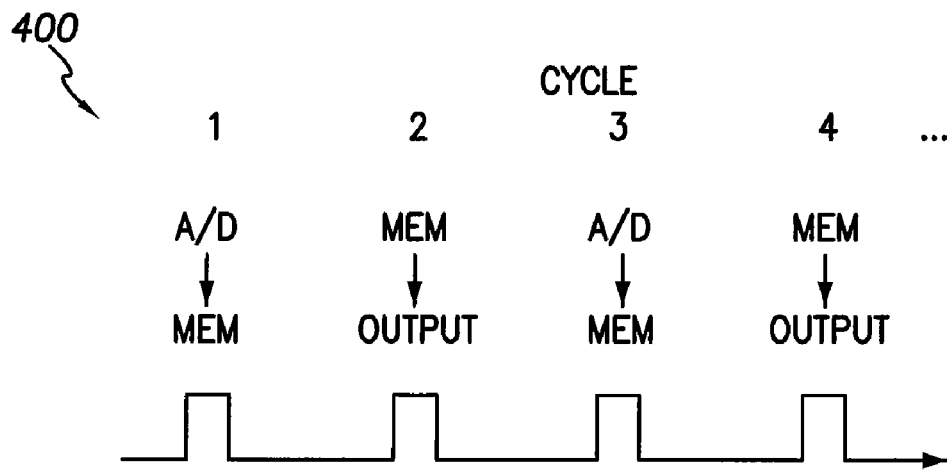
FIG. 8 is a timing diagram illustrating a series of pulses that may be used to sequentially power and control the sensors of FIGS. 1-7.
Figure 9:
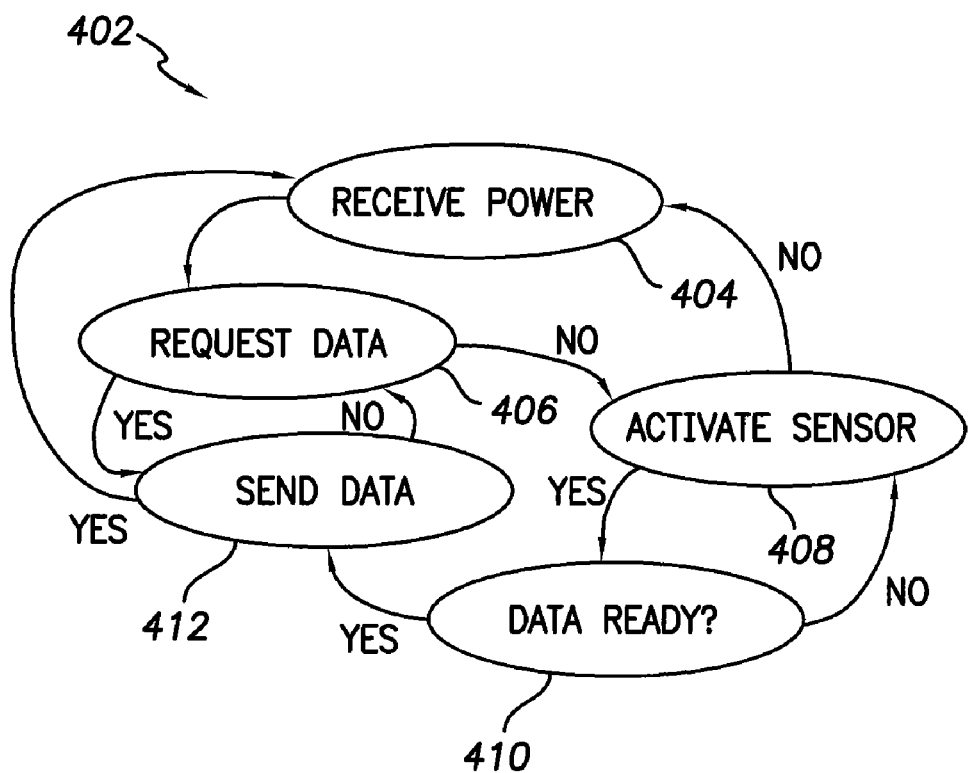
FIG. 9 is a state diagram illustrating a series of states that may be employed by the sensors of FIGS. 1-7 to sequentially power and control the sensor.

Turning now to FIGS. 8 and 9, techniques for powering and controlling sensors based on a sequence of pulses will be described. These techniques are primarily provided to accommodate sensors that require more power or more time than accommodated during a single EPP or IMP. FIG. 8 is a timing diagram 400 illustrating a simple example wherein the sensor is equipped to operate in two states. In a first state, the sensor senses a physiological parameter, converts an analog (i.e. voltage) signal representative of the parameter into digital data and then stores that data within sensor memory. In the second state, the sensor outputs the data, i.e. the sensor reads the data from memory (or from a hardware output or a memory register, and modulates it for transmission to the pacer/ICD. As such, during a first cycle of FIG. 8, the sensor senses a first value of the physiological parameter and stores that first value in memory. During a second cycle, the sensor transmits the value to the pacer/ICD. During a third cycle, the sensor senses a second value of the parameter and stores that second value in memory. During a fourth cycle, the sensor transmits that second value to the pacer/ICD. This process repeats indefinitely with the sensor alternating between sensing parameters and transmitting the sensed parameters. In this manner, a sensor that is not capable of both sensing and transmitting data in a single cycle (either because there is insufficient power within a single pulse or because the sensor needs more time to both sense and transmit the data) can still be exploited. Note that the timing diagram of FIG. 8 only illustrates the control pulses that power and control the sensor. Any intervening pacing pulses are omitted. Note also that the control pulses need not be uniformly paced as shown. In some cases, the amount of time between successive control pulses will vary considerably. For example, if the pace/ICD is configured to apply EPP control pulses only in a demand pacing mode, then a fair amount of time may elapse between successive EPP pulses, particularly if the patient does not require much demand pacing.

FIG. 9 is a state diagram 402 illustrating a more complex example wherein the sensor requires a greater number of cycles to sense and transmit data. In an initial "power receive" state 404, the sensor awaits receipt of a next EPP (or IMP) control pulse. In response to the next EPP, the sensor stores the power delivered in the pulse using, e.g., a capacitive storage device within the sensor. The sensor then transitions to a "request data" state 406. Upon receipt of the next EPP, the sensor determines whether its memory still stores any unsent data from a previous measurement. Such a determination may be performed by examining an appropriate internal flag. Assuming there is no unsent data, the sensor then transitions to an "activate sensor" state 408. Upon receipt of the next EPP, the sensor activates its sensing components to begin measuring whatever physiological parameter the sensor is designed to measure. In some cases, the sensor will require more power than it presently possesses in order to make the measurement. If so, the sensor then transitions back to the receive power state 404 for receipt and storage of additional power via another EPP, before returning to the activate sensor state via the data access state. Some sensors may require power from several EPPs (or IMPs) before the sensors can activate its measurement components and so states 404, 406 and 408 may be cycled through repeatedly. Eventually, the sensor will have stored enough power to properly activate its measurement components and the sensor will then transition to a "data ready" state 410.

Upon receipt of the next EPP, the sensor determines whether data is ready for transmission, i.e. whether the measurement components of the sensor have completed their measurement. In some cases, the sensor may require additional time and/or power to complete a single measurement. If so, the sensor transitions back to activate sensor state 408. Some sensors may require several measurement cycles before the sensor can complete its measurement and so states 408 and 410 may be cycled through repeatedly. Eventually, the sensor completes its measurement and so the sensor then transitions from the data ready state to a "send data" state 412. Upon receipt of the next EPP, the sensor transmits all or a portion of the data to the pacer/ICD. If the sensor is cable of transmitting all data that had been measured in a single cycle, then the sensor simply transitions back to the power receive state to begin receiving power for the next measurement. Otherwise, the sensor transitions back to the data request state. Since at least some data remains to be sent, the sensor then transitions back to the send data state. This process repeats until all data is transmitted.

Thus, FIG. 9 sets forth a state diagram for a generalized sensor design that can accommodate the need to employ multiple cycles to power the sensor, to complete measurements and/or to transmit the data. Numerous other sensor designs are, of course, consistent with the invention. In general, the invention may be implemented using at least two approaches. In the first approach, one may develop a generalized structure that can be applied to different types of sensors and for each type of sensor allows customization of the hardware and/or software. In the second approach, one may simply design customized hardware and software for each type of sensor.

Exemplary Sensor Circuitry

Figure 10:
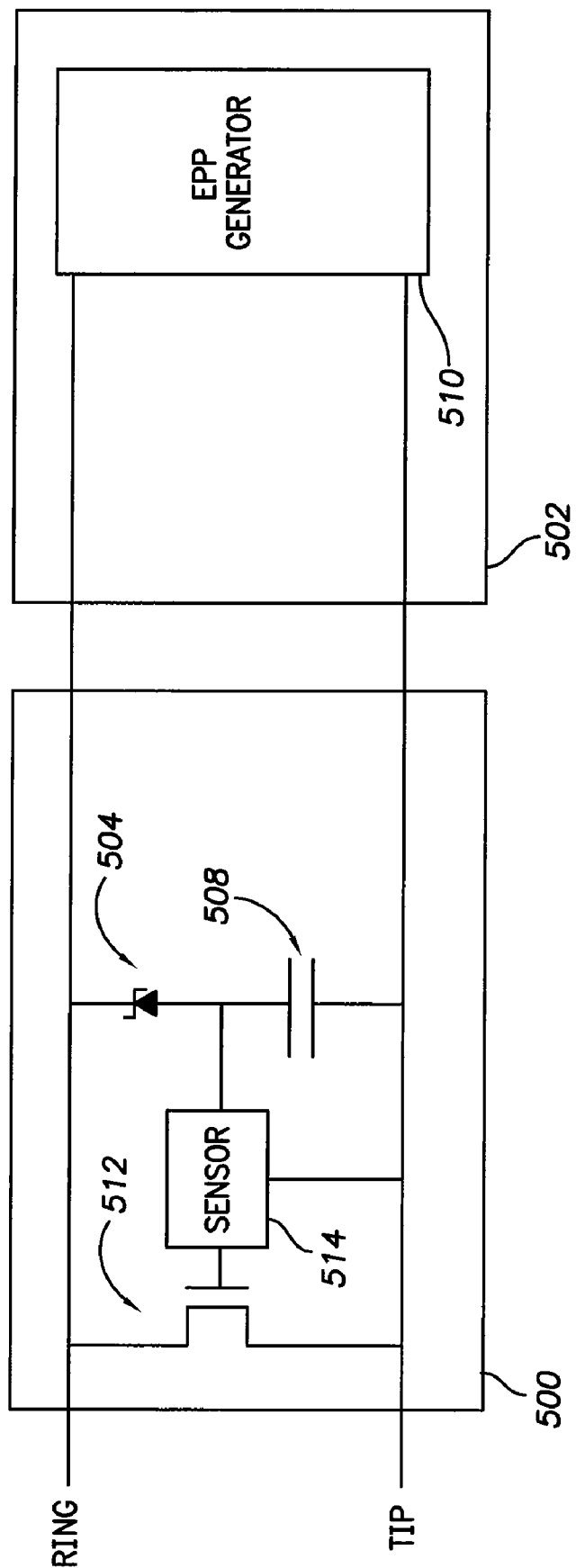
FIG. 10 is a circuit schematic, partly in block diagram form, illustrating a sensing circuit particularly designed for use with EPPs.
Figure 11:
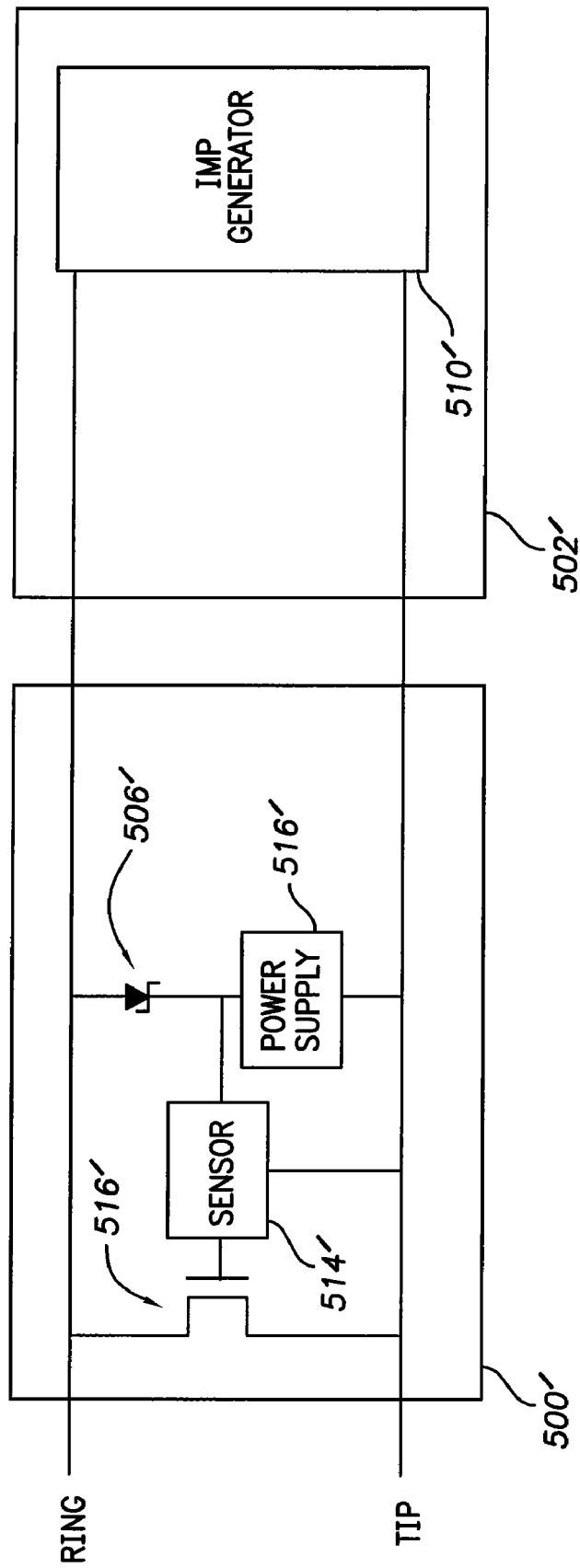
FIG. 11 is a circuit schematic, partly in block diagram form, illustrating a sensing circuit particularly designed for use with IMPs.
Figure 12:
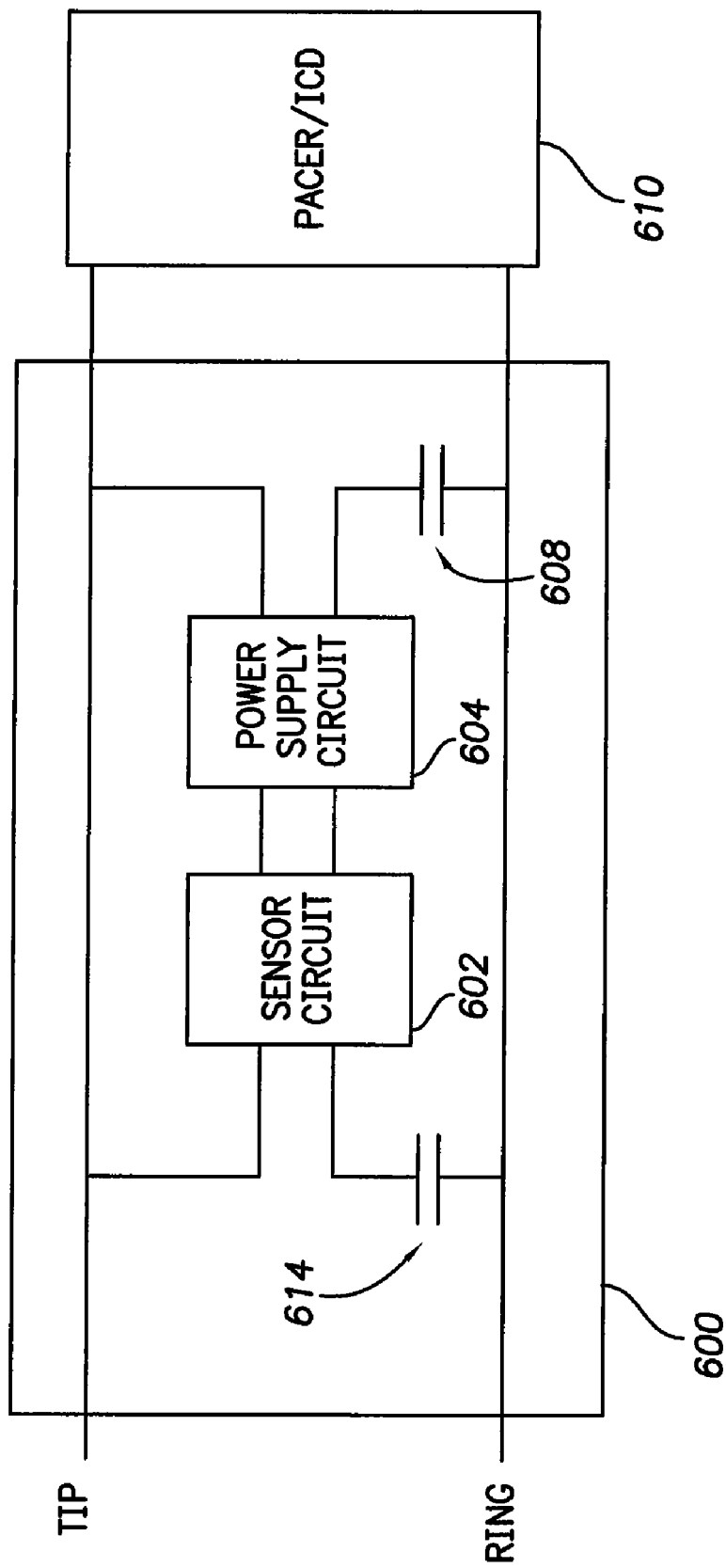
FIG. 12 is a circuit schematic, partly in block diagram form, illustrating a sensing circuit that is capacitively coupled to a lead.

FIGS. 10-12 illustrate exemplary circuit designs for use with a sensor mounted to a bipolar lead. Suitable modifications can be made to accommodate sensors for mounting to unipolar leads. Referring first to FIG. 10, a circuit 500 for use with EPPs is schematically illustrated along with pertinent portions of a pacer/ICD 502. Circuit 500 includes a breakdown diode (i.e. Zener diode) 504 used principally for voltage regulation. A capacitor 508 holds charge received via an EPP generated by an EPP generator 510 of the pacer/ICD. A transistor 512 controls the data transmission of the sensor 514, which senses a physiological parameter using energy, stored in the capacitor. The sensor also includes internal components for outputting the sensed parameter. Note that the sensor is only activated in response to a sufficiently high voltage applied through the Zener diode, thereby ensuring the sensor only responds to an EPP of sufficiently high amplitude. As shown in FIG. 10, the various components of circuit 500 are connected between tip and ring lead conductors. Note that, in this particular implementation, tip is more negative than ring. Note also that the tip and ring lead conductors can be more generally referred to as first and second electrodes.

Referring next to FIG. 11, a circuit 500' for use with IMPs is schematically illustrated along with pertinent portions of a pacer/ICD 502. Circuit 500' includes a Schottky type diode 506' used principally for voltage regulation. A power supply circuit 516', which may contain a capacitor, holds charge received via an IMP generated by an IMP generator 510' of the pacer/ICD. A transistor 512' controls the data transmission of the sensor 514', which senses a physiological parameter using power stored in the power supply circuit. The sensor also includes internal components for outputting the sensed parameter. Note that the sensor will only be activated in response to IMPs delivered between the ring and case, or IMPs of sufficiently high current. The various components of circuit 500' of FIG. 11 are connected between tip and ring lead conductors. As with the implementation of FIG. 10, tip is more negative than ring. Again, the tip and ring lead conductors can be more generally referred to as first and second electrodes.

FIG. 12 illustrates a circuit design that provides capacitive coupling and isolation for a sensor circuit. A sensor 600 includes a sensor circuit 602 and a separate power supply circuit 604. A first capacitor 608 couples AC power from a pacer/ICD 610 into the power supply circuit. A second capacitor 614 couples output signals from the sensor circuitry to the pacer/ICD. This design is well suited for use with pacer/ICDs that provide power to the sensor via a high frequency signals (and also uses high frequency signals for data transmission.) The frequency band (B1) of the power signal is typically within 10-50 kHz. The output signal of the sensor is transmitted at a different frequency band (B2) back to the main unit also via capacitive coupling.

Figure 13:
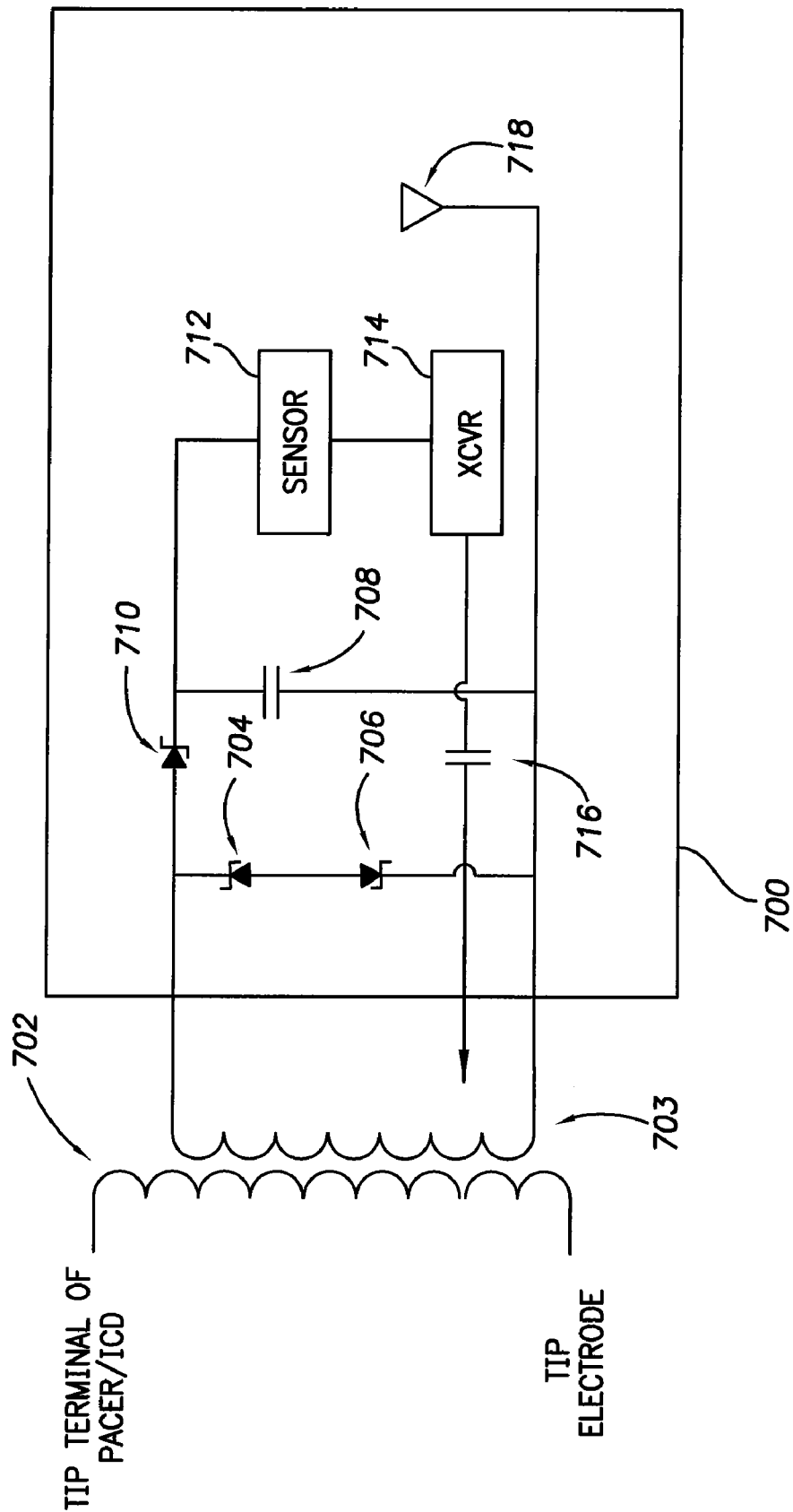
FIG. 13 is a circuit schematic, partly in block diagram form, illustrating a sensing circuit that derives power from a lead using electromagnetic induction.

FIG. 13 illustrates a sensor circuit design wherein power is inductively coupled into the sensor from a unipolar or bipolar lead. This design also incorporates defibrillation protection, i.e. protection from high voltage defibrillation pulses delivered via a coil electrode on the same lead. The circuit 700 is inductively coupled to tip or ring conductor(s) via a pair of inductors 702, 703. Note inductor 702 is made by the lead itself. The tip or ring wire in the lead has a significant amount of inductance. To increase the inductance, magnetic/Ferrite coating may be applied on the coils. Defibrillation protection is provided via breakdown diodes 704, 706. Charge is stored via a capacitor 708. A third Schottky diode 710 is provided to aid in voltage rectification. A sensor module 712 senses the actual physiological parameter of interest. A transceiver (XCVR) 714 in combination with another capacitor 716 control data transmission. In this particular example, transmission can be performed through inductive coupling, or using a wireless transmitter 718. This design may be exploited either using an integrated sensor (wherein the sensor is fabricated as a component of the lead) or as a slip-on sensor, as will be described in the next section.

Slip-on Sensor Designs

Figure 14:
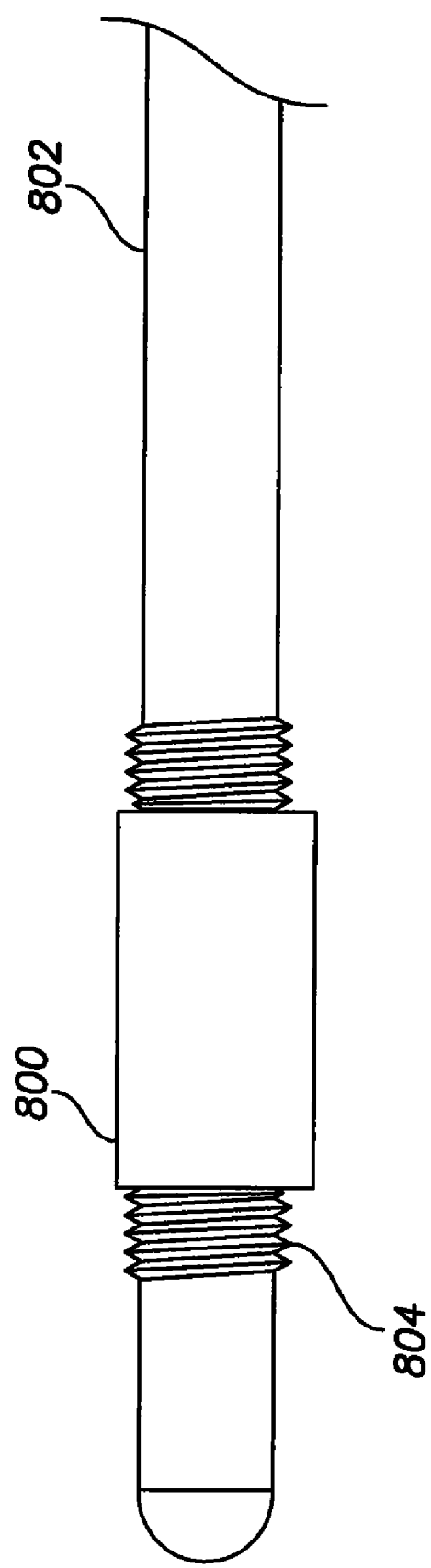
FIG. 14 is an elevational view of a portion of a unipolar lead wherein a snap-on/slip-on sensor is mounted to the lead.

FIG. 14 illustrates a slip-on sensor design wherein the sensor is not fabricated as a component of the lead but is instead mounted to the exterior housing or sheath of an otherwise conventional unipolar or bipolar lead. In the particular example of FIG. 14, a slip-on sensor 800 is installed on a unipolar lead 802. Coil 804 of the sensor receives power via induction from the unipolar conductor of the lead whenever power signals (i.e. IMPs) are transmitted along the lead. A sensor design of the type already described with reference to FIG. 13 may be used. Preferably, the slip-on sensor is securely mounted to the lead so that there is no risk that it might become detached during use. Note that, since there is no direct connection to the conductors within the lead, this design may employ capacitive or inductive, or wireless data transmission to the pacer/ICD. Alternatively, an output device as described above with reference to FIGS. 1 and 2 may be used, which utilizes a tissue return path to transmit signals to the pacer/ICD. (These devices are not shown in FIG. 13 but are integrated components of sensor 800.) Hence, even if the snap-on/slip-on sensor is used with a bipolar lead, the data output techniques for unipolar leads discussed above may nevertheless be employed. Note also that multiple sensors can be mounted to the housing of a single lead. Unique IDs may be employed to allow the pacer/ICD to distinguish output signals from the various sensors. As can be appreciated, the slip-on design is particularly advantageous as it allows sensors to be added to otherwise conventional leads so that the lead design need not be changed. It also allows the user to customize a sensor array for a particular patient at implant.

What have been described are various designs for adding sensors to leads without requiring additional conductors within the leads. Although described primarily with respect to sensors, it should be understood that actuators may alternatively be used, such as implantable drug pumps.

For the sake of completeness, a detailed description of an exemplary pacer/ICD incorporating leads with sensors will now be provided. The general techniques of the invention, however, may be performed using any suitable implantable medical devices.

Exemplary Pacer/ICD

Figure 15:
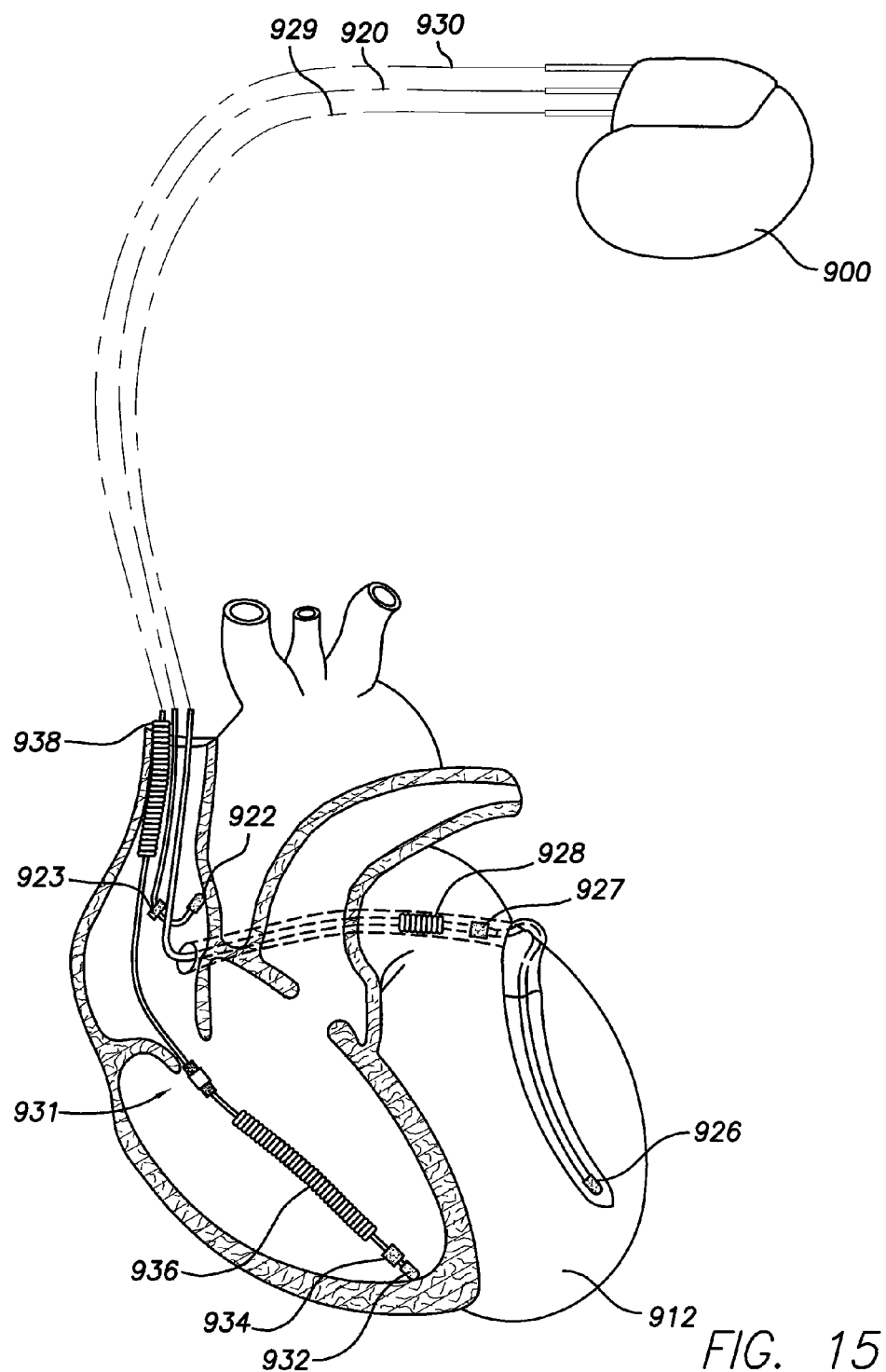
FIG. 15 is a simplified, partly cutaway view, illustrating an exemplary pacer/ICD shown along with a full set of leads implanted in the heart of the patient, and particularly illustrating a snap-on/slip-on sensor as in FIG. 14.
Figure 16:
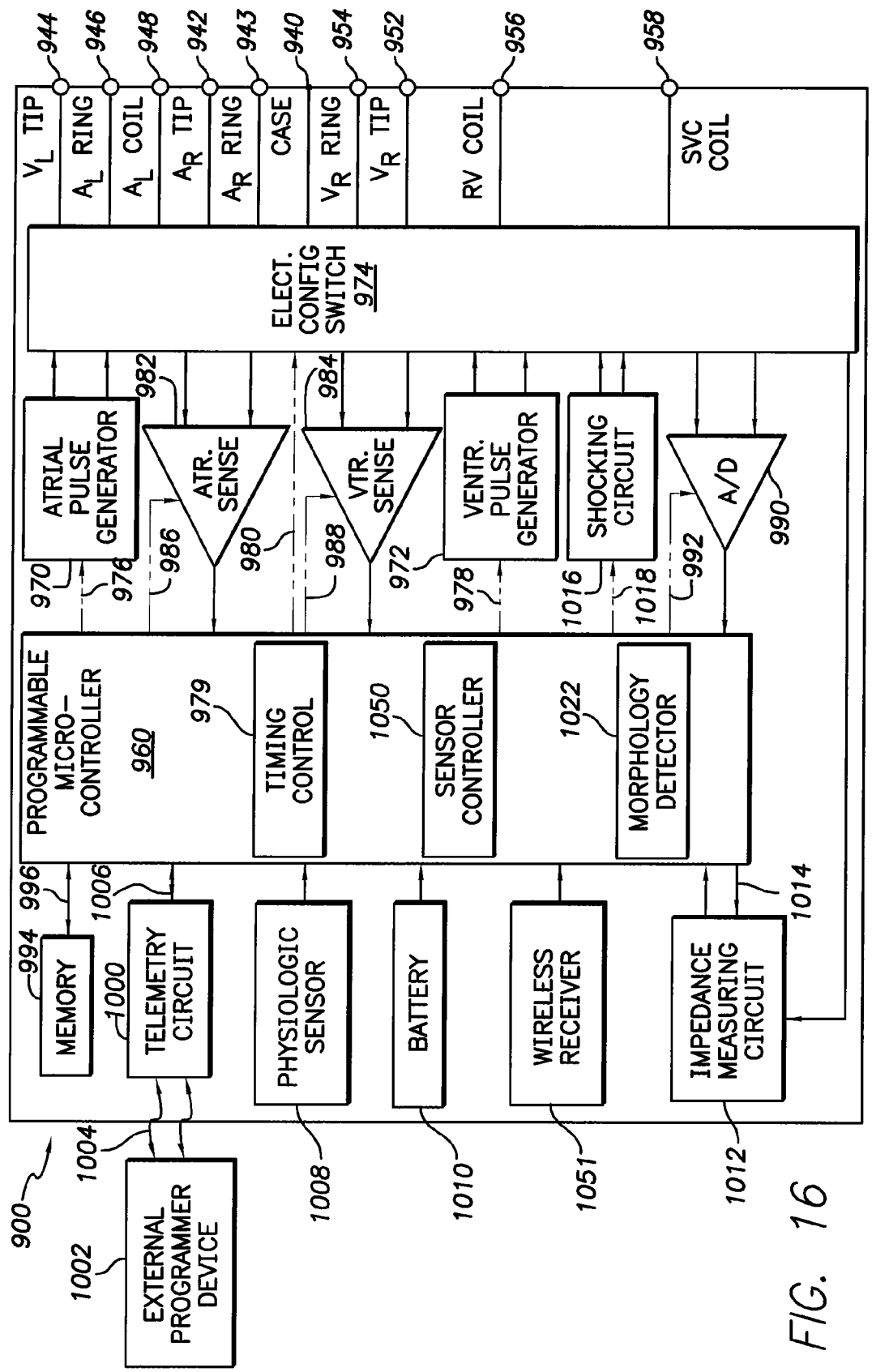
FIG. 16 is a functional block diagram of the pacer/ICD of FIG. 15, illustrating basic circuit elements that provide cardioversion, defibrillation and/or pacing stimulation in four chambers of the heart.

With reference to FIGS. 15 and 16, a description of an exemplary pacer/ICD will now be provided. FIG. 15 provides a simplified diagram of the pacer/ICD, which is a dual-chamber stimulation device capable of treating both fast and slow arrhythmias with stimulation therapy, including cardioversion, defibrillation, and pacing stimulation.

To provide atrial chamber pacing stimulation and sensing, pacer/ICD 900 is shown in electrical communication with a heart 912 by way of a right atrial lead 920 having an atrial tip electrode 922 and an atrial ring electrode 923 implanted in the atrial appendage. Pacer/ICD 900 is also in electrical communication with the heart by way of a right ventricular lead 930 having, in this embodiment, a ventricular tip electrode 932, a right ventricular ring electrode 934, a right ventricular (RV) coil electrode 936, and a superior vena cava (SVC) coil electrode 938. Typically, the right ventricular lead 930 is transvenously inserted into the heart so as to place the RV coil electrode 936 in the right ventricular apex, and the SVC coil electrode 938 in the superior vena cava. Accordingly, the right ventricular lead is capable of receiving cardiac signals, and delivering stimulation in the form of pacing and shock therapy to the right ventricle.

Lead 930 also includes a snap-on/slip-on sensor 931 of the type described above with reference to FIG. 14 and equipped to transmit signals back to the pacer/ICD via inductive coupling or wireless communication. Alternatively, the leads may be configured to exploit sensor using any of the other designs discussed above. Although only a single snap-on/slip-on sensor is shown mounted to lead 930, two or more sensors may instead be mounted. Also, the other leads may additionally, or alternatively, employ sensors as well.

To sense left atrial and ventricular cardiac signals and to provide left chamber pacing therapy, pacer/ICD 900 is coupled to a "coronary sinus" lead 929 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 929 is designed to receive atrial and ventricular cardiac signals and to deliver left ventricular pacing therapy using at least a left ventricular tip electrode 926, left atrial pacing therapy using at least a left atrial ring electrode 927, and shocking therapy using at least a left atrial coil electrode 928. With this configuration, biventricular pacing can be performed. Although only three leads are shown in FIG. 15, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 900 is shown in FIG. 16. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 940 for pacer/ICD 900, shown schematically in FIG. 16, is often referred to as the "can", "case" or "case electrode" and may be programmably selected to act as the return electrode for all "unipolar" modes. The housing 940 may further be used as a return electrode alone or in combination with one or more of the coil electrodes, 928, 936 and 938, for shocking purposes. The housing 940 further includes a connector (not shown) having a plurality of terminals, 942, 943, 944, 946, 948, 952, 954, 956 and 958 (shown schematically and, for convenience, the names of the electrodes to which they are connected are shown next to the terminals).

As such, to achieve right atrial sensing and pacing, the connector includes at least a right atrial tip terminal ($A_R$ TIP) 942 adapted for connection to the atrial tip electrode 922 and a right atrial ring ($A_R$ RING) electrode 943 adapted for connection to right atrial ring electrode 923. To achieve left chamber sensing, pacing and shocking, the connector includes at least a left ventricular tip terminal ($V_L$ TIP) 944, a left atrial ring terminal ($A_L$ RING) 946, and a left atrial shocking terminal ($A_L$ COIL) 948, which are adapted for connection to the left ventricular ring electrode 926, the left atrial tip electrode 927, and the left atrial coil electrode 928, respectively. To support right chamber sensing, pacing and shocking, the connector further includes a right ventricular tip terminal ($V_R$ TIP) 952, a right ventricular ring terminal ($V_R$ RING) 954, a right ventricular shocking terminal ($R_V$ COIL) 956, and an SVC shocking terminal (SVC COIL) 958, which are adapted for connection to the right ventricular tip electrode 932, right ventricular ring electrode 934, the RV coil electrode 936, and the SVC coil electrode 938, respectively.

At the core of pacer/ICD 900 is a programmable microcontroller 960, which controls the various modes of stimulation therapy. As is well known in the art, the microcontroller 960 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 960 includes the ability to process or monitor input signals (data) as controlled by a program code stored in a designated block of memory. The details of the design and operation of the microcontroller 960 are not critical to the invention. Rather, any suitable microcontroller 960 may be used that carries out the functions described herein. The use of microprocessor-based control circuits for performing timing and data analysis functions are well known in the art.

As shown in FIG. 16, an atrial pulse generator 970 and a ventricular pulse generator 972 generate pacing stimulation pulses for delivery by the right atrial lead 920, the right ventricular lead 930, and/or the coronary sinus lead 929 via an electrode configuration switch 974. It is understood that in order to provide stimulation therapy in each of the four chambers of the heart, the atrial and ventricular pulse generators, 970 and 972, may include dedicated, independent pulse generators, multiplexed pulse generators or shared pulse generators. The pulse generators, 970 and 972, are controlled by the microcontroller 960 via appropriate control signals, 976 and 978, respectively, to trigger or inhibit the stimulation pulses.

The microcontroller 960 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 974 includes a plurality of switches for connecting the desired electrodes to the appropriate I/O circuits, thereby providing complete electrode programmability. Accordingly, the switch 974, in response to a control signal 980 from the microcontroller 960, determines the polarity of the stimulation pulses (e.g., unipolar, bipolar, combipolar, etc.) by selectively closing the appropriate combination of switches (not shown) as is known in the art.

Atrial sensing circuits 982 and ventricular sensing circuits 984 may also be selectively coupled to the right atrial lead 920, coronary sinus lead 929, and the right ventricular lead 930, through the switch 974 for detecting the presence of cardiac activity in each of the four chambers of the heart. Accordingly, the atrial (ATR. SENSE) and ventricular (VTR. SENSE) sensing circuits, 982 and 984, may include dedicated sense amplifiers, multiplexed amplifiers or shared amplifiers. The switch 974 determines the "sensing polarity" of the cardiac signal by selectively closing the appropriate switches, as is also known in the art. In this way, the clinician may program the sensing polarity independent of the stimulation polarity. Each sensing circuit, 982 and 984, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 900 to deal effectively with the difficult problem of sensing the low amplitude signal characteristics of atrial or ventricular fibrillation. The outputs of the atrial and ventricular sensing circuits, 982 and 984, are connected to the microcontroller 960 which, in turn, are able to trigger or inhibit the atrial and ventricular pulse generators, 970 and 972, respectively, in a demand fashion in response to the absence or presence of cardiac activity in the appropriate chambers of the heart.

For arrhythmia detection, pacer/ICD 900 utilizes the atrial and ventricular sensing circuits, 982 and 984, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 960 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 990. The data acquisition system 990 is configured to acquire intracardiac electrogram signals, convert the raw analog data into a digital signal, and store the digital signals for later processing and/or telemetric transmission to an external device 1002. The data acquisition system 990 is coupled to the right atrial lead 920, the coronary sinus lead 929, and the right ventricular lead 930 through the switch 974 to sample cardiac signals across any pair of desired electrodes. The microcontroller 960 is further coupled to a memory 994 by a suitable data/address bus 996, wherein the programmable operating parameters used by the microcontroller 960 are stored and modified, as required, in order to customize the operation of pacer/ICD 900 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 900 may be non-invasively programmed into the memory 994 through a telemetry circuit 1000 in telemetric communication with the external device 1002, such as a programmer, transtelephonic transceiver or a diagnostic system analyzer. The telemetry circuit 1000 is activated by the microcontroller by a control signal 1006. The telemetry circuit 1000 advantageously allows intracardiac electrograms and status information relating to the operation of pacer/ICD 900 (as contained in the microcontroller 960 or memory 994) to be sent to the external device 1002 through an established communication link 1004. Pacer/ICD 900 further includes an accelerometer or other physiologic sensor 1008, commonly referred to as a "rate-responsive" sensor because it is typically used to adjust pacing stimulation rate according to the exercise state of the patient. However, the physiological sensor 1008 may further be used to detect changes in cardiac output, changes in the physiological condition of the heart, or diurnal changes in activity (e.g., detecting sleep and wake states) and to detect arousal from sleep. Accordingly, the microcontroller 960 responds by adjusting the various pacing parameters (such as rate, AV Delay, V-V Delay, etc.) at which the atrial and ventricular pulse generators, 970 and 972, generate stimulation pulses. While shown as being included within pacer/ICD 900, it is to be understood that the physiologic sensor 1008 may also be external to pacer/ICD 900, yet still be implanted within or carried by the patient. A common type of rate responsive sensor is an activity sensor incorporating an accelerometer or a piezoelectric crystal, which is mounted within the housing 940 of pacer/ICD 900. Other types of physiologic sensors are also known, for example, sensors that sense the oxygen content of blood, respiration rate and/or minute ventilation, pH of blood, ventricular gradient, etc. Physiological sensor 1008 is in addition to any sensors mounted within the leads using the techniques described above.

The pacer/ICD additionally includes a battery 1010, which provides operating power to all of the circuits shown in FIG. 16. The battery 1010 may vary depending on the capabilities of pacer/ICD 900. If the system only provides low voltage therapy, a lithium-based cell may be utilized. For pacer/ICD 900, which employs shocking therapy, the battery 1010 must be capable of operating at low current drains for long periods, and then be capable of providing high-current pulses (for capacitor charging) when the patient requires a shock pulse. The battery 1010 must also have a predictable discharge characteristic so that elective replacement time can be detected. Accordingly, pacer/ICD 900 is preferably capable of high voltage therapy and appropriate batteries.

As further shown in FIG. 16, pacer/ICD 900 is shown as having an impedance measuring circuit 1012, which is enabled by the microcontroller 960 via a control signal 1014. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 1012 is advantageously coupled to the switch 974 so that any desired electrode may be used.

In the case where pacer/ICD 900 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 960 further controls a shocking circuit 1016 by way of a control signal 1018. The shocking circuit 1016 generates shocking pulses of low (up to 0.5 joules), moderate (0.5-10 joules) or high energy (11 to 40 joules), as controlled by the microcontroller 960. Such shocking pulses are applied to the heart of the patient through at least two shocking electrodes, and as shown in this embodiment, selected from the left atrial coil electrode 928, the RV coil electrode 936, and/or the SVC coil electrode 938. The housing 940 may act as an active electrode in combination with the RV electrode 936, or as part of a split electrical vector using the SVC coil electrode 938 or the left atrial coil electrode 928 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 10-40 joules), delivered asynchronously (since R-waves may be too disorganized), and pertaining exclusively to the treatment of fibrillation. Accordingly, the microcontroller 960 is capable of controlling the synchronous or asynchronous delivery of the shocking pulses.

The microcontroller also includes a sensor controller 1050 operative to selectively control the operations of sensor 931 of FIG. 15 using techniques already described. In particular, the sensor controller is operative to modulate selected characteristics of electrical pulses delivered to the leads so as to control operations of physiological sensors (or actuators) mounted to the leads. Sensor controller 1050 also process output signals generated by the sensor, which are received, in this example, by a wireless receiver 1051. Wireless receiver 1051 is shown as being an internal component of the pacer/ICD. As can be appreciated, it preferably includes at least one antenna (not separately shown) that is located on the pacer/ICD for receiving the wireless signals. In implementations where the output signals are relayed back to the pacer/ICD via patient tissue or via the return conductor of the lead, the various sensing components of the pacer/ICD are modified as needed to sense the output signals and to foreword them to the sensor controller for processing. Note also that the pulse generators and the electrical configuration switch of the pacer/ICD may be modified as needed to accommodate EPPs in addition to conventional low voltage pacing pulses.

Figure 17:
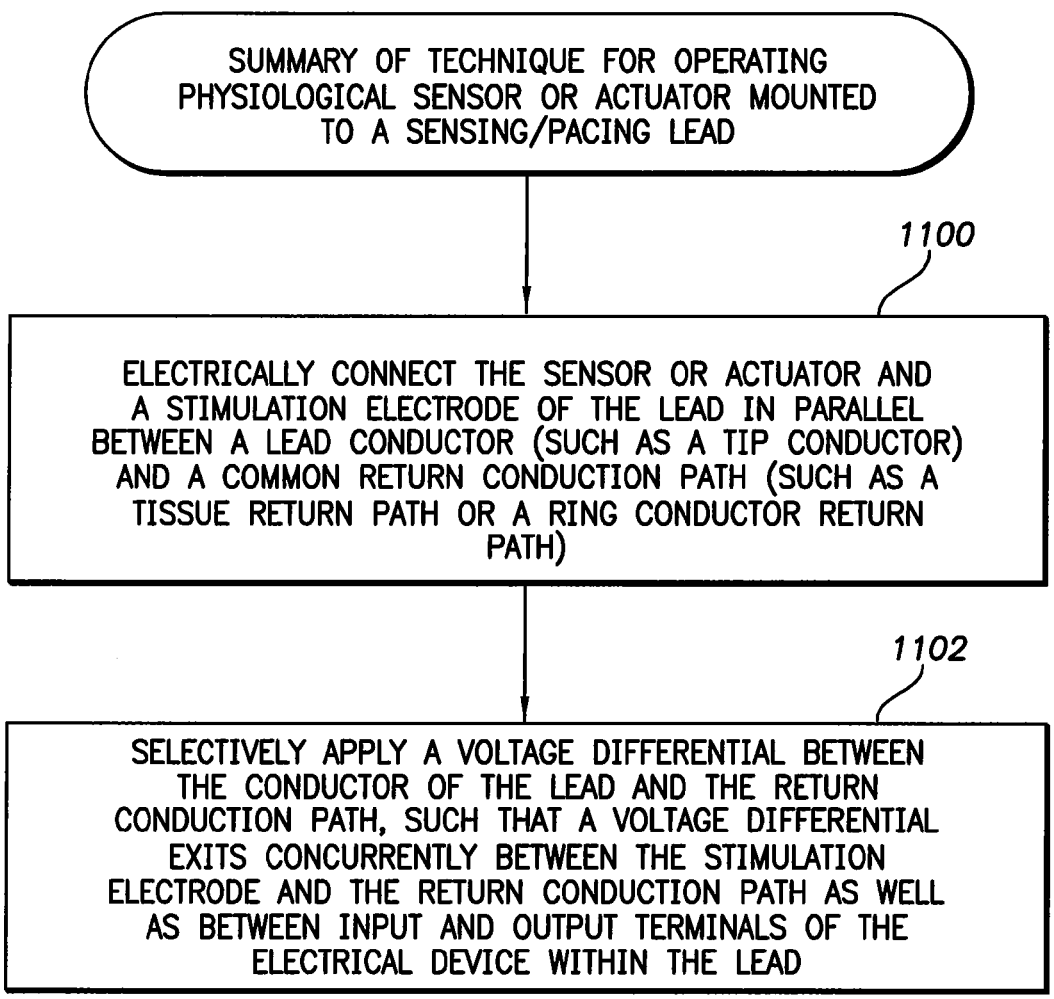
FIG. 17 is a flow chart summarizing exemplary method techniques of the invention.

For the sake of completeness, the general method of the invention is summarized in the flowchart of FIG. 17. Briefly, at step 1100, the sensor or actuator of the lead and a stimulation electrode of the lead are electrically connected in parallel between a lead conductor (such as a tip conductor) and a common return conduction path (such as a tissue return path or a ring conductor return path). At step 1102, a voltage differential is selectively applied between the conductor of the lead and the return conduction path, such that a voltage differential exits concurrently between the stimulation electrode and the return conduction path as well as between input and output terminals of the electrical device within the lead. Exemplary techniques for implementing these general method steps have already been described above with reference to the preceding figures.

Figure 18:
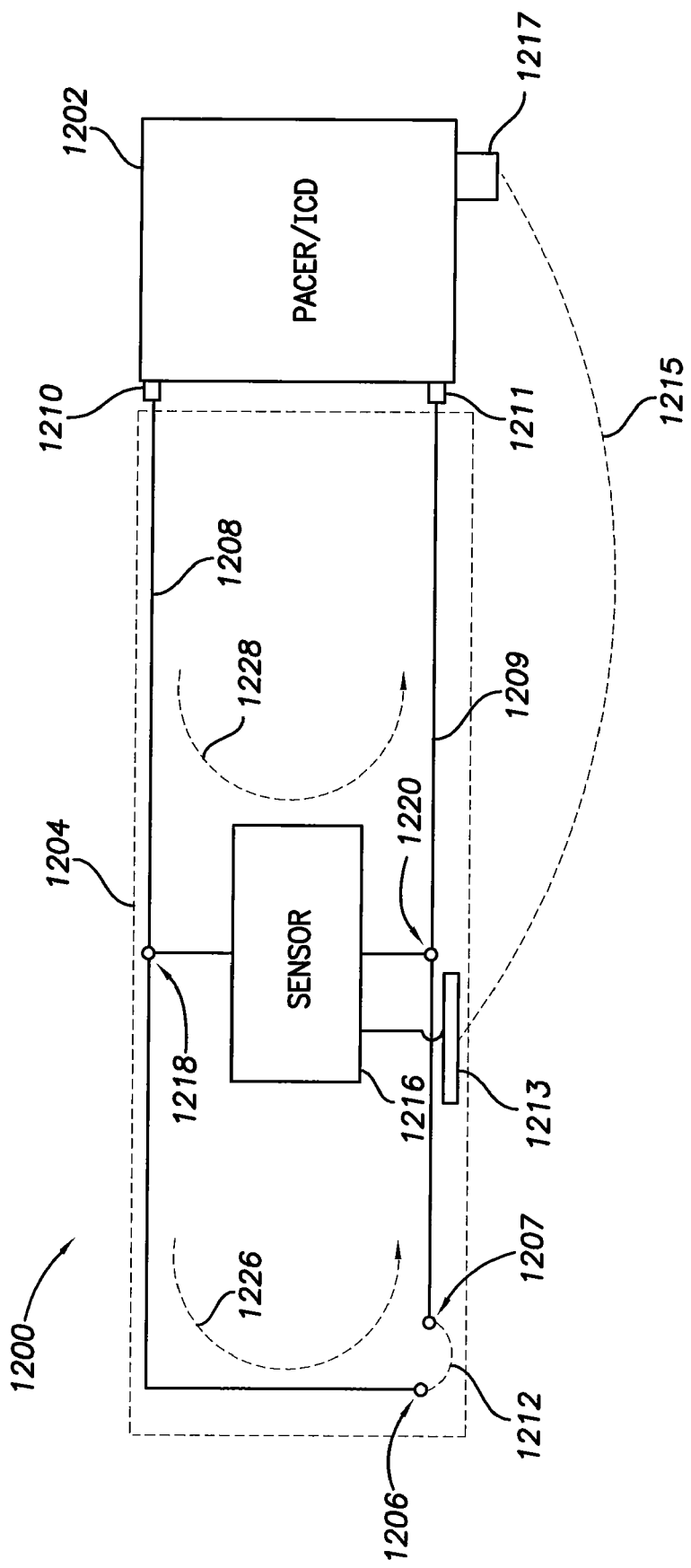
FIG. 18 is a block diagram, partly in schematic form, illustrating another bipolar lead implementation of the invention wherein a three-terminal sensor is mounted to the lead.

Finally, it should be understood that sensors or other electrical devices having three of more terminals might also be employed. This is shown in FIG. 18, which schematically illustrates an implantable system 1200 having a pacer/ICD or other implantable medical device 1202 and a bipolar lead 1204. The bipolar lead includes a tip electrode 1206 connected to the pacer/ICD via a tip conductor 1208 coupled to a tip connector or terminal 1210 of the pacer/ICD. The bipolar lead also includes a ring electrode 1207 connected to the pacer/ICD via a ring conductor 1209 coupled to a ring connector or terminal 1211 of the pacer/ICD. Again, for generality, the tip and ring electrodes may also be referred to herein as "first" and "second" electrodes. Depending upon the particular implementation, the first electrode may be more negative than the second, or vice versa. A first conducting path 1212 from the tip electrode 206 to a ring electrode 207 is provided through cardiac tissue or other patient tissue. A three-terminal physiological sensor 1216 has a first (input) terminal 1218 connected to the tip conductor, a second (ground) terminal 1220 connected to the ring conductor, and a third (output) terminal connected to a sensor output electrode 1213, which is positioned adjacent patient tissue. A current return path from the sensor to the pacer/ICD is provided from terminal 1220 along ring conductor 1209; whereas an output signal path 1215 is provided from the sensor to a device case electrode 1217 of the pacer/ICD through patient tissue. (Device case electrode 1217 may be the same electrode as case electrode 940 of FIG. 16.)

As with the implementation of FIG. 5, two primary current paths are thereby provided between tip terminal 1220 and ring terminal 1211 so that the current divides between them and later reunites within the pacer/ICD. A first path 1226 passes along the tip conductor to the tip electrode, then passes through patient tissue before returning to the pacer/ICD via the ring electrode and the ring conductor. A second path 1228 passes along the tip conductor through the sensor and back to the pacer/ICD via the ring conductor. (Depending upon the polarity, current may instead flow in the opposite direction.) Electrical pacing pulses can be selectively delivered to the patient tissue by routing at least a portion of the current along path 1226. The sensor can be selectively activated to sense physiological parameters of interest within the patient tissue by routing at least a portion of the current along path 1228. Output signals from the sensor are sent to the pacer/ICD from sensor output terminal 1213 to device case electrode 1217 along tissue path 1215 using any suitable transmission technique, such as the PWM or PCM techniques discussed above. Other multiple terminal sensors (or other multiple terminal electrical devices) may be used where appropriate, including devices having four or more terminals. It should be understood that, under the broad definition of the term "in parallel" set forth above, these multiple terminal embodiments provide an electrical device connected in parallel with the tip and ring electrodes, even though the electrical device itself has more than two terminals.

What have been described are various exemplary systems and methods for use in a pacer/ICD. Principles of the invention may be exploited using other implantable systems or in accordance with other techniques. Thus, while the invention has been described with reference to particular exemplary embodiments, modifications can be made thereto without departing from the scope of the invention. Note also that the term "including" as used herein is intended to be inclusive, i.e. "including but not limited to."

What is claimed is:

1. A lead for use with an implantable medical device for implant within patient tissue, the lead comprising:
   a stimulation electrode fitted to be positioned adjacent patient tissue;
   a conductor operative to conduct electrical current from the implantable medical device through the lead to the stimulation electrode, the current returning to the implantable medical device along a return conduction path; and
   a sensor disposed within the lead and connected between the conductor and the return conduction path so that the sensor and the stimulation electrode are connected in parallel between the conductor and the return path;
   wherein the sensor is configured to be activated only in response to enhanced pacing pulses which exceed an activation threshold and wherein the stimulation electrode is configured to be activated only in response to pacing pulses which are below the activation threshold such that current is selectively directed either through the stimulation electrode or through the sensor.

2. The lead of claim 1 wherein the sensor is one or more of a blood oxygen sensor, a pH sensor, a temperature sensor, a blood glucose sensor, an accelerometer, a cardiac output sensor, a contractility sensor, an acoustic sensor and a pressure sensor.

3. The lead of claim 1 wherein the sensor of the lead is an actuator.

4. The lead of claim 3 wherein the actuator is an implantable drug pump.

5. The lead of claim 1 wherein the stimulation electrode is a first electrode and the return conduction path to the implantable medical device is through patient tissue, so that a unipolar lead is provided having a sensor and a first electrode connected in parallel between a conductor within the lead and a return path within patient tissue.

6. The lead of claim 1 wherein the stimulation electrode is a first electrode connected to a first electrode conductor within the lead and wherein the return conduction path includes a second electrode connected to a second electrode conductor within the lead, so that a bipolar lead is provided having a sensor and an electrode pair connected in parallel between a first electrode conductor and a second electrode conductor within the lead.

7. The lead of claim 1 wherein the sensor of the lead is configured to be activated only in response to a voltage exceeding a predetermine threshold voltage, so that any electrical pulses delivered by the implantable medical device at voltages less than that threshold do not activate the sensor.

8. The lead of claim 1 wherein the sensor of the lead is configured to be activated only in response to a pulse having a pulse width exceeding a predetermine threshold width, so that any electrical pulses delivered by the implantable medical device with widths less than that threshold do not activate the sensor.

9. The lead of claim 1 wherein the sensor of the lead is configured to respond to a sequence of electrical pulses delivered by the implantable medical device.

10. The lead of claim 9 wherein the sensor of the lead is a physiological sensor configured to respond to a first pulse by sensing physiological parameters and to respond to a second pulse by transmitting the physiological parameters to the device.

11. The lead of claim 1 wherein the sensor of the leads is a physiological sensor equipped to transmit sensed signals to the implantable medical device via wireless communication.

12. The lead of claim 1 wherein the sensor of the leads is a physiological sensor equipped to transmit sensed signals to the implantable medical device via non-wireless communication along the return conduction path.

13. The lead of claim 1 wherein the physiological sensor is mounted externally to the lead and is equipped to receive power inductively from the lead.

\* \* \* \* \*